US012424310B2

(12) United States Patent
 Neumann

(10) Patent No.: US 12,424,310 B2
(45) Date of Patent: Sep. 23, 2025

(54) SYSTEMS AND METHODS FOR GENERATING A DENTAL NOURISHMENT PROGRAM

(71) Applicant: KPN INNOVATIONS, LLC., Lakewood, CO (US)

(72) Inventor: Kenneth Neumann, Lakewood, CO (US)

(73) Assignee: KPN INNOVATIONS LLC, Lakewood, CO (US)

( * ) Notice: Subject to any disclaimer, the term of this patent is extended or adjusted under 35 U.S.C. 154(b) by 1037 days.

(21) Appl. No.: 17/164,385

(22) Filed: Feb. 1, 2021

(65) Prior Publication Data

US 2022/0246272 A1    Aug. 4, 2022

(51) Int. Cl.
 *G06Q 10/00* (2023.01)
 *G16H 20/60* (2018.01)
 *G16H 50/50* (2018.01)

(52) U.S. Cl.
 CPC ............. *G16H 20/60* (2018.01); *G16H 50/50* (2018.01)

(58) Field of Classification Search
 CPC ............................... G16H 20/60; G16H 50/50
 See application file for complete search history.

(56) References Cited

U.S. PATENT DOCUMENTS

| 10,246,753 | B2 | 4/2019 | Apte |
| 10,468,140 | B2 | 11/2019 | Wright |
| 2018/0010171 | A1 | 1/2018 | Mougeot |
| 2018/0374581 | A1 | 12/2018 | Berringer |
| 2019/0138690 | A1 | 5/2019 | Adams |
| 2019/0172555 | A1 | 6/2019 | Apte |
| 2020/0381116 | A1 | 12/2020 | Pingali |

FOREIGN PATENT DOCUMENTS

| WO | 2020018954 A1 | 1/2020 |
| WO | 2020168015 A1 | 8/2020 |

OTHER PUBLICATIONS

Web Site: vol. 60, 2020—Issue 13; https://doi.org/10.1080/10408398. 2019.1630600 Title: The impact of oral rehabilitation coupled with healthy dietary advice on the nutritional status of adults: A systematic review and meta-analysis Date: By: McGowan.

*Primary Examiner* — Rajesh Khattar
(74) *Attorney, Agent, or Firm* — Caldwell Intellectual Property Law

(57) ABSTRACT

A system for generating a dental nourishment program includes a computing device configured to receive at least a dental factor, retrieve, a dental parameter, generate, using the dental parameter, an alimentary model, wherein the alimentary model includes determining a respective effect of each alimentary level of a plurality of alimentary levels on the dental parameter, generating the alimentary model as a function of the respective effect, identify, using the alimentary model, a plurality of alimentary elements, develop, using plurality of alimentary elements, a hygienic model, wherein the hygienic model includes determining, a plurality of hygienic patterns relating dental hygiene in relation to consumption of the plurality of alimentary elements, developing the hygienic model as a function of the hygienic patterns and the plurality of alimentary elements, and build a dental nourishment program using the hygienic model and the nutritional model.

16 Claims, 9 Drawing Sheets

SYSTEMS AND METHODS FOR GENERATING A DENTAL NOURISHMENT PROGRAM

FIELD OF THE INVENTION

The present invention generally relates to the field of nutrition planning for dental disorders. In particular, the present invention is directed to systems and methods for generating a dental nourishment program.

BACKGROUND

Efficient systems for enumerating dental-related data are stymied from difficulties in adequately sampling the breadth of physiological parameters that relate to dental-related phenomenon over the lifetime of the subject. Furthermore, systems have difficulty in efficiently and properly developing algorithms for targeting the ways in which superficial and health-based manipulation of the smile can occur, capturing the amounts of change, and predicting dental trajectories from these confounding variables.

SUMMARY OF THE DISCLOSURE

In an aspect, a system for generating a dental nourishment program using machine-learning includes a computing device configured to receive at least a dental factor relating to a subject, retrieve, using the dental factor, a dental parameter related to the subject, generate, using the dental parameter, an alimentary model, wherein generating the alimentary model includes determining a respective effect of each alimentary level of a plurality of alimentary levels on the dental parameter, and generating the alimentary model as a function of the respective effect of the plurality of alimentary levels, identify, using the alimentary model, a plurality of alimentary elements, develop, using the plurality of alimentary elements, a hygienic model, wherein developing the hygienic model includes determining, using the plurality of alimentary elements, a plurality of hygienic patterns relating dental hygiene in relation to consumption of the plurality of alimentary elements, and developing the hygienic model as a function of the hygienic patterns and the plurality of alimentary elements, and build a dental nourishment program using the hygienic model and the nutritional model.

In another aspect, a method for generating a dental nourishment program using machine-learning, the method includes receiving, by a computing device, at least a dental factor relating to a subject, retrieving, by the computing device, using the dental factor, a dental parameter related to the subject, generating, by the computing device, using the dental parameter, an alimentary model, wherein generating the alimentary model includes determining a respective effect of each alimentary level of a plurality of alimentary levels on the dental parameter, and generating the alimentary model as a function of the respective effect of the plurality of alimentary levels, identifying, by the computing device, using the alimentary model, a plurality of alimentary elements, developing, by the computing device, using the plurality of alimentary elements, a hygienic model, wherein developing the hygienic model includes determining, using the plurality of alimentary elements, a plurality of hygienic patterns relating dental hygiene in relation to consumption of the plurality of alimentary elements, and developing the hygienic model as a function of the hygienic patterns and the plurality of alimentary elements, and building, by the computing device, a dental nourishment program using the hygienic model and the nutritional model.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations, and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for generating a dental nourishment program. In an embodiment, system includes a computing device configured to retrieve a dental parameter. Computing device may receive dental factor relating to a subject and may retrieve and/or generate a dental parameter, for instance using a machine-learning model and training data, which provides a scoring function that provides a metric which relates both superficial and health-based factors. Computing device may use at least a dental parameter to classify a subject to a dental grouping, which may include a classification to nutrition-linked conditions which may be addressed with specific nutritional modification. Computing device is configured to generate an alimentary model, for instance using a machine-learning algorithm, training data and the dental parameter input, to determine effects of nutrient levels on dental parameter. Computing device is configured to use the alimentary model to identify a plurality of alimentary elements using the respective effect relating to each nutrient level. Computing device is configured to develop a hygienic model, for instance using a machine-learning algorithm, training data, and the plurality of alimentary elements. Hygienic model may be configured to optimize alimentary element consumption alongside dental hygiene, for instance using a linear programming function. Computing device is configured to build a dental nourishment program using the alimentary model and the hygienic model. Generating dental nourishment program may include generating a dental index, which may communicate dental health as a function of what the subject consumes.

Figure 1:
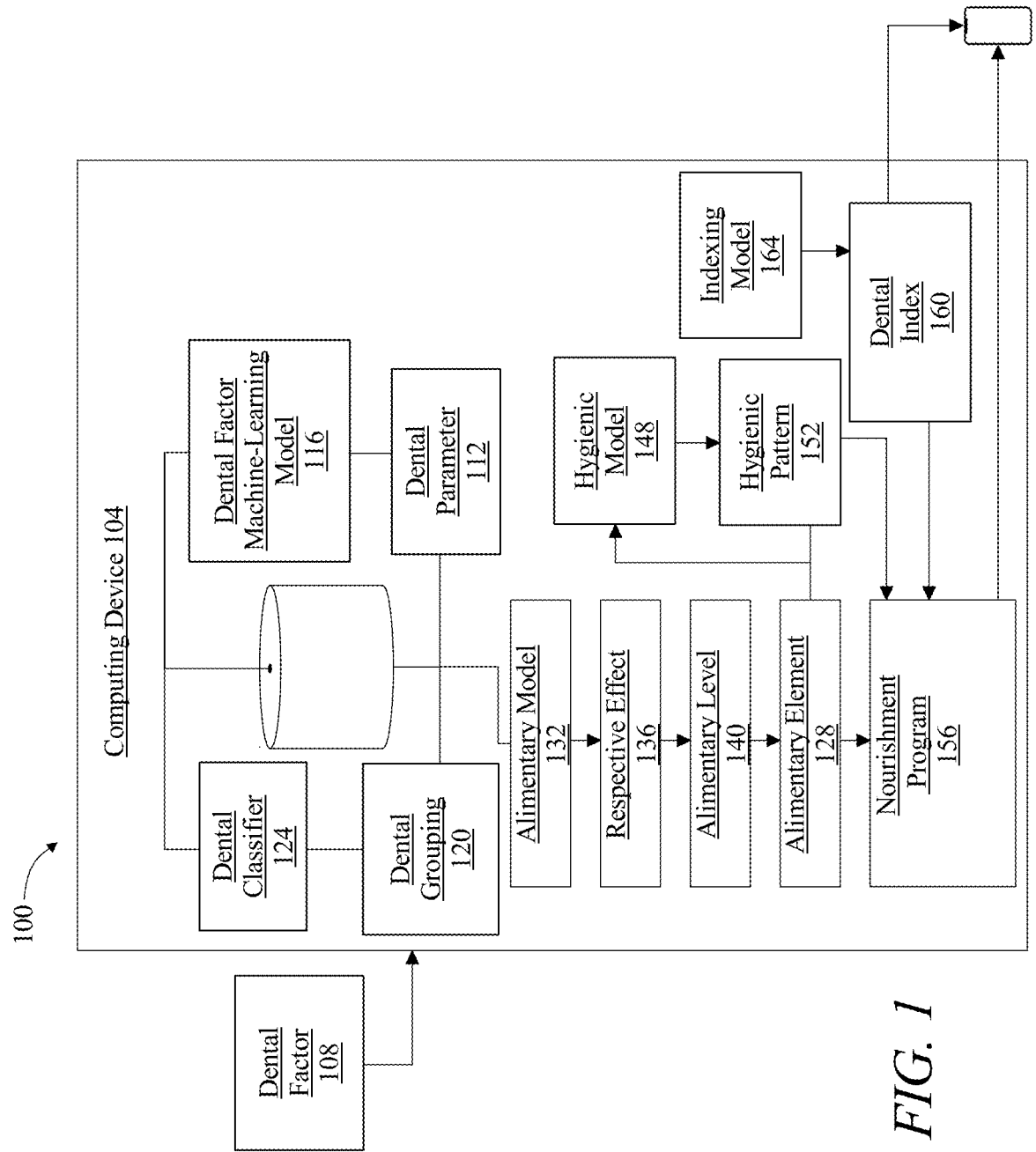
FIG. 1 is a block diagram illustrating an exemplary embodiment of a system for generating a dental nourishment program.

Referring now to FIG. 1, an exemplary embodiment of a system 100 for generating a dental nourishment program is illustrated. System includes a computing device 104. Computing device 104 may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Computing device 104 may include a single computing device operating independently, or may include two or more computing device operating in concert, in parallel, sequentially or the like; two or more computing devices may be included together in a single computing device or in two or more computing devices. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus, or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software, and the like) may be communicated to and/or from a computer and/or a computing device. Computing device 104 may include but is not limited to, for example, a computing device or cluster of computing devices in a first location and a second computing device or cluster of computing devices in a second location. Computing device 104 may include one or more computing devices dedicated to data storage, security, distribution of traffic for load balancing, and the like. Computing device 104 may distribute one or more computing tasks as described below across a plurality of computing devices of computing device, which may operate in parallel, in series, redundantly, or in any other manner used for distribution of tasks or memory between computing devices. Computing device 104 may be implemented using a "shared nothing" architecture in which data is cached at the worker, in an embodiment, this may enable scalability of system 100 and/or computing device.

With continued reference to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Continuing in reference to FIG. 1, computing device is configured to receive at least a dental factor relating to a subject. A "dental factor," as used in this disclosure, is a datum describing a biological and/or chemical substance or process that is indicative of oral and/or dental health. Dental factor 108 may include any biological and/or chemical substance or process that is indicative of and/or relating to tooth decay, enamel thickness and/or weakening, gum health, oral microbiome, gingivitis, periodontitis, infection of the mouth, tongue, throat, tonsils, adenoids, sinus cavity, and the like. Dental factor 108 may include diagnoses indicating one or more oral and/or dental diseases such as gingivitis, halitosis, periodontal disease, dental caries, cavities, tooth loss, oral cancer, canker sores, oral herpes, herpangina, thrush, oral gonorrhea, hand-foot-and-mouth disease, fungal infections, bacterial infections, viral infections, oro-dental trauma, noma, cleft lip, xerostomia, candidiasis, denture stomatitis, plaque, tartar, and/or any other mouth-associated condition. Dental factor 108 may include biochemical markers of dental function and appearance, including superficial categories which may and/or may not be indicative of an underlying health issue such as tooth color, bite shape, symmetricalness of teeth, cleanliness of tongue, odor of breath, and the like. Dental factor 108 may include biological molecules originating from the subject existing within a normal cell, a stressed cell, disease state cell, and/or a specific response of the body indicative of tooth deterioration, gum pain, tooth loosening, misalignment, and the like.

Continuing in reference to FIG. 1, receiving the at least a dental factor 108 may include receiving a result of one or more tests relating to the subject. Dental factor 108 may include test results of screening and/or early detection of tooth decay, cavities, fluoride treatment, diagnostic procedures such as X-rays, casting of tooth molds and dental impressions, oral health exams, oral cancer exams, symptoms identified by subject such as tooth pain, bleeding or swollen gums, alterations to the tongue such as changes in color or texture, growths within the mouth, deteriorating gums, signs of illness within the mouth such as infections, and the like. Dental factor 108 may include imaging, such as visible-spectrum, optical imaging of the teeth, mouth, tongue, and the like, which can capture and communicate the appearance of the oral cavity. Dental factor 108 may include physiological, chemical, and biological data and/or data relating to biomolecules associated with oral and/or dental functioning such as salivary parameters and biomarkers, including pH, buffering capacity of saliva, relative viscosity, salivary flow rates, presence of amino acids and amino acid metabolism such as arginine and urea, proteins such as salivary albumin levels, proline-rich proteins, and mucin-family proteins, enzymes such as alkaline phosphatase, amylase, Proteinase 3, and super oxide dismutase, bacterial isolates such as pathogenic subspecies, commensal bacterial isolates, antioxidants, nutrient levels of the subject for instance for calcium, phosphorous, copper, zinc, and the like.

Continuing in reference to FIG. 1, dental factor 108 may include results and or analysis enumerating the identification of nucleic acid sequences. Dental factor 108 may include the presentation of single nucleotide polymorphisms (SNPs), mutations, chromosomal deletions, inversions, translocation events, and the like, in genetic sequences. Dental factor 108 may include epigenetic factors indicative of rates of disease, disorder, tooth decay, among other dental issues such as expression patterns of microRNAs (miRNAs), SNPs/mutation in genes relating to storage of calcium and phosphorous for teeth, silencing of genes and/or protein production relating to the maintenance of a heathy appearance of the throat, tongue, oral epithelial, gums, and/or teeth, among other epigenetic events. Dental factor 108 may include the consequences of genetic manipulation such as gene silencing on protein expression. Dental factor 108 may be received as a function of a subject indicating a prior diagnosis, treatment received, among other data indicated in a medical history, physical assessment, and the like, for instance enamel weakening from chemotherapy regimen, persistent nutritional deficiency, among other factors. Dental factor 108 may include any symptoms, side effects, and co-morbidities associated with and relating to aging, treatment regimens, recovery from injury and/or illness, and the like. Dental factor 108 may be received and/or identified from a biological extraction of a subject, which may include analysis of a physical sample of a subject such as blood, DNA, saliva, and the like, without limitation and as described in U.S. Nonprovisional application Ser. No. 16/886,647, filed May 28, 2020, and entitled, "METHODS AND SYSTEMS FOR DETERMINING A PLURALITY OF BIOLOGICAL OUTCOMES USING A PLURALITY OF DIMENSIONS OF BIOLOGICAL EXTRACTION USER DATA AND ARTIFICIAL INTELLIGENCE," the entirety of which is incorporated herein by reference.

Continuing in reference to FIG. 1, dental factor 108 may be received by computing device 104 via the subject and/or a secondary source. Secondary source may include another individual such as a physician, lab technician, dentist, orthodontist, caretaker, dietician, guardian, and the like. Dental factor 108 may be received as raw data from a wearable device, medical device, and/or physiological sensor intended to gather data relating to subject such as a pedometer, bioimpedance monitoring, ECG/EKG/EEG data, blood pressure monitor, blood sugar and volatile organic compound (VOC) monitor, and the like. Dental factor 108 may be received via a web browser and the Internet. Dental factor 108 may be received from a second electronic device and/or computing device, for instance as a transmission from a client device, device located at a dentist, and the like. Dental factor 108 may be received via a database such as a NOSQL database, as described in further detail below.

Continuing in reference to FIG. 1, dental factor 108 may be organized into training data sets. "Training data," as used herein, is data containing correlations that a machine learning process, algorithm, and/or method may use to model relationships between two or more categories of data elements. For instance, and without limitation, training data may include a plurality of data entries, each entry representing a set of data elements that were recorded, received, and/or generated together; data elements may be correlated by shared existence in a given data entry, by proximity in a given data entry, or the like. Multiple data entries in training data may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data according to various correlations; correlations may indicate causative and/or predictive links between categories of data elements, which may be modeled as relationships such as mathematical relationships by machine learning processes as described in further detail below.

Continuing in reference to FIG. 1, dental factor 108 may be used to generate training data for a machine-learning process. A "machine learning process," as used in this disclosure, is a process that automatedly uses a body of data known as "training data" and/or a "training set" to generate an algorithm (such as a collection of one or more functions, equations, and the like) that will be performed by a machine-learning module to produce outputs given data provided as inputs; this is in contrast to a non-machine learning software programing where the commands to be executed are determined in advance by a subject and written in a programming language, as described in further detail below.

Continuing in reference to FIG. 1, dental factor 108 may be organized into training data sets and stored and/or retrieved by computing device 104, without limitation, as a relational database, a key-value retrieval database such as a NOSQL database, or any other format or structure for use as a database that a person skilled in the art would recognize as suitable upon review of the entirety of this disclosure. Dental factor 108 training data may alternatively or additionally be implemented using a distributed data storage protocol and/or data structure, such as a distributed hash table and the like. Dental factor 108 training data may include a plurality of data entries and/or records, as described above. Data entries may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries of dental factors may be stored, retrieved, organized, and/or reflect data and/or records as used herein, as well as categories and/or populations of data consistent with this disclosure.

Continuing in reference to FIG. 1, computing device is configured to retrieve, using the dental factor 108, a dental parameter related to the subject. A "dental parameter," as used in this disclosure, is a parameter that enumerates both the superficial and health-based factors of the subject's smile and dental health as a function of dental factor(s) 108. For instance and without limitation, dental parameter 112 may include a "smile score" which indicates a score that communicates the current tooth color, gum-to-tooth ratio, enamel thickness, breath odor, tongue appearance, and the like, as a function of a scoring function and a plurality of dental factors 108. Such a dental parameter 112 may include a scoring range, with a maximal score and a minimal score, wherein incrementation is determined as a function of changes in dental factors 108. Dental factors 108 may change as a function of changes in dental hygiene, subject nutrition, dental cleaning, orthodontics, changes in diet, smoking, alcohol consumption, among others lifestyle factors.

Continuing in reference to FIG. 1, dental parameter 112 may include a relative scoring scale compared to a theoretical level of according to what is scientifically achievable for an individual, wherein the parameter may provide an objective numerical value that properly enumerates dental health and appearance, and the parameter may be tracked with a scoring function. Such a dental parameter 112 may include a function, or a series of values, plotted as a function of a variable which describes the dental parameter 112, for instance as a function of a biomarker, nutritional deficiency level, microbiome, dental hygiene product usage, teeth cleaning, among other dental factors 108. Dental parameter 112 may include an amount of dental factor 108 as it relates to a threshold value, for instance and without limitation, a range of values of dental factor 108 in a cohort of healthy subjects. Dental parameter 112 may include an arbitrary numerical value which is assigned according to a scoring function which may be derived by, for instance and without limitation, a machine-learning model which assigns a numerical value to the parameter according to a theoretical maximal value, minimal value, wherein the scoring incrementation is generated as a function of the range. Dental parameter 112 may be biologic-specific, for instance and without limitation, a parameter for each of 100+ types of dental factor 108 categories, where each parameter communicates a likelihood that a dental factor 108 relates to a particular dental disorder, for instance as the dental factor 108 relates to a 'healthy range'.

Continuing in reference to FIG. 1, dental parameter 112 may include qualitative and/or quantitative summarization of the presence of symptomology, development of dental disorder, biomarkers indicative of disease, current rates of pain and/or discomfort, lifetime risk of tooth loss, decay, caries, and the like, associated with current dental factor(s) 108, biomarkers classified to subcategories, and the like. Dental parameter 112 may include qualitative determinations, such as binary "yes"/"no" determinations for particular degradation types, "normal"/"abnormal" determinations about the presence of and/or concentration of dental factors 108, for instance as compared to a normalized threshold value of a biomarker among healthy adults. Dental parameter 112 may include a plurality of dental parameters, wherein dental parameters are quantitative determinations such as a "smile index", which may include any metric, parameter, or numerical value that communicates the current state of dental appearance and health according to nutritional integrity, symptoms, among other dental factors 108. Dental parameter 112 may include dental parameters that are mathematical expressions relating the current dental degradation state.

Continuing in reference to FIG. 1, retrieving dental parameter 112 may include a process of searching for, locating, and returning dental parameter 112 data. For example, dental parameter 112 may be retrieved as documentation on a computer to be viewed or modified such as files in a directory, database, and the like. In non-limiting illustrative embodiments, computing device 104 may locate and download dental parameter 112 via a web browser and the Internet, receive as input via a software application and a client device, and the like. Computing device 104 may retrieve dental parameter 112 from a database, as described in further detail below.

Continuing in reference to FIG. 1, retrieving dental parameter 112 may include receiving data via a graphical user interface. A "graphical user interface," as used in this disclosure, is any form of a user interface that allows a subject to interface with an electronic device through graphical icons, audio indicators, text-based interface, typed command labels, text navigation, and the like, wherein the interface is configured to provide information to the subject and accept input from the subject. Graphical user interface may accept input, wherein input may include an interaction (such as a questionnaire) with a client device. A client device, as described in further detail below, may include computing device 104, a "smartphone," cellular mobile phone, desktop computer, laptop, tablet computer, internet-of-things (IOT) device, wearable device, among other devices. Client device may include any device that is capable for communicating with computing device 104, database, or able to receive data, retrieve data, store data, and/or transmit data, for instance via a data network technology such as 3G, 4G/LTE, 5G, Wi-Fi (IEEE 802.11 family standards), and the like. Client device may include devices that communicate using other mobile communication technologies, or any combination thereof, for short-range wireless communication (for instance, using Bluetooth and/or Bluetooth LE standards, AirDrop, Wi-Fi, NFC, and the like), and the like.

Still referring to FIG. 1, retrieving the dental parameter 112 related to the subject may include training a dental factor machine-learning model with training data including a plurality of data entries correlating dental factors 108 to dental parameters 112. Computing device 104 may generate the dental parameter 112 as a function of the dental factor machine-learning model and the at least a dental factor 108. Dental factor machine-learning model 116 may include any machine-learning process, algorithm, and/or model as performed by machine-learning module, described in further detail below. Generating dental parameter 112 as a function of training data and a machine-learning model may be performed, without limitation, as described in Ser. No. 17/000,929, filed Aug. 24, 2020, titled "METHOD OF AND SYSTEM FOR IDENTIFYING AND AMELIORATING BODY DEGRADATIONS," the entirety of which is incorporated herein by reference. Particular body degradations may be related to tooth loss, development of cavities, enamel weakening, among other physiological deteriorations associated with the oral cavity, in the subject. Dental factor machine-learning model 116 may be generated an output of dental parameter 112 from dental factor 108, which includes an objective enumeration of tooth appearance in the subject. From such a dental parameter 112 a diagnosis regarding the 'type' or 'category' of dental disorder, such as the presence of plaque and cavities, and finally a relationship between the dental factor 108 and the disorder(s) that subject may experience enumerated in dental parameter 112 according to the model. This way, the model could relate a proposed number of cavities and/or amount of plaque relative to the dental factors 108.

Continuing in reference to FIG. 1, relationships observed in training data to enumerate dental parameter 112 may be used to determine cross-body deterioration and/or disease, wherein degradation from one instance may be statistically related to dental degradation for which no directly observable data exists, for instance and without limitation, as described in Ser. No. 17/000,973, filed Aug. 24, 2020, titled "A METHOD OF AND SYSTEM FOR IDENTIFYING AND ENUMERATING CROSS-BODY DEGRADATIONS," the entirety of which is incorporated herein by reference. In such an instance, degradation due to nutritional deficiencies, which originates in a first location may manifest in the mouth according to a relationship identified in cross-body degradation. Such a cross-body pain relationship may include eating disorders such as anorexia, bulimia, overeating, obesity, metabolic disorders, and the like, may manifest as degradation in the oral cavity.

Continuing in reference to FIG. 1, training data for dental factor machine-learning model 116 may include dental factors 108 organized into training data sets, as described herein, including results from biological extraction samples, health state questionnaires regarding symptomology, medical histories, physician assessments, lab work, oral exams, dental imaging, radiology, dental impressions, and the like, organized by test category and/or result. Training data may be retrieved from a database, as described in further detail below. Dental factor machine-learning model 116 training data may originate from the subject, for instance via a questionnaire and a user interface with computing device 104, for subject to provide medical history data and/or symptoms. Receiving dental parameter training data may include receiving whole genome sequencing, gene expression patterns, and the like, for instance as provided by a genomic sequencing entity, hospital, database, the Internet, and the like. Training data may include raw data values recorded and transmitted to computing device 104 via a wearable device and/or physiological sensor data which may be used for determining if a subject tis experiencing pain and/or discomfort, for instance and without limitation, capturing heart rate, pulse, breathing rate, bioimpedance data relating to swelling and/or water retention, blood pressure, blood monitoring for sugar, vitamins, electrolytes, trace minerals, volatile carbon compounds (VOCs) on the breath, and the like. Training data may originate from an individual other than subject, including for instance a physician, lab technician, nurse, dietician, strength coach, psychologist, and the like. Training data may be retrieved by computing device for instance for instance via a web browser and the Internet, such as via a telemedicine platform, data repository, dental health monitoring application, mobile phone, and the like. It is important to note that training data for machine-learning processes, algorithms, and/or models used within system 100 herein may likewise originate from any source described for dental factor machine-learning model 116 training data.

Continuing in reference to FIG. 1, dental factor machine-learning model 116 may include any machine-learning algorithm such as K-nearest neighbors algorithm, a lazy naïve Bayes algorithm, among other algorithms, machine-learning process such as supervised machine-learning, unsupervised machine-learning, or method such as neural nets, deep learning, and the like. Dental factor machine-learning model 116 may be trained to derive an equation, function, series of equations, or any mathematical operation, relationship, or heuristic, that can automatedly accept an input, such as dental factor(s) 108, and correlate, classify, or otherwise calculate an output, such as dental parameter(s) 112. Dental factor machine-learning model 116 may derive individual functions, derived for unique relationships observed from the training data for each dental factor 108, or combinations thereof. In non-limiting illustrative examples, training data may include numerical data involved in a variety of physiological tests, as described above, may be retrieved from a database, such as a repository of peer-reviewed research (e.g. National Center for Biotechnology Information as part of the United States National Library of Medicine), and the dental factor machine-learning model 116 may derive an algorithm which determines an average and statistical evaluation (mean±S.D.) derived from the trained data, across which the subject's dental parameters 112 may be compared. In such an example, dental factor machine-learning model 116 may derive an algorithm according to the data used to derive the average and statistical evaluation changes as a function of the subset of data to which the subject is to be compared, for instance and without limitation, based on differentiating factors such as age, fitness level, nutrition deficiency, symptomology, past diagnoses, and the like.

Continuing in reference to FIG. 1, retrieving the dental parameter 112 may include training a dental classifier using a dental classification machine-learning process and training data including a plurality of data entries of dental parameter data from a subset of categorized subjects, and classifying the dental parameter to a dental grouping using the dental classifier. A "dental grouping," as used in this disclosure, is a determination about a cause and/or contributing factor concerning a dental state, oral disease, and the like, of a subject. Dental grouping 120 may include a designation of a physiological degradation type which relates to some level and/or cause of pain and/or discomfort originating from dental disease. Dental grouping 120 may include tissue, organ, and/or biological system designation such as "enamel damage", "exposed dentin and/or pulp", "root damage", "tooth decay", and the like, which may be the underlying cause of the pain and/or discomfort. Dental grouping 120 may include a designation regarding a disease type that may not involve a particular tissue such as "gingivitis", "halitosis", "periodontitis", and the like. Dental grouping 120 may include pathological, histological, and/or clinical classification identifiers such as "periodontitis scale of 5 mm", where a periodontal probe is used to measure the depth of the tooth socket for determining gingivitis and/or periodontitis, "dental health score of 10", "moderate tooth decay", "2 existing cavities", and the like. Dental grouping 120 may include identifiers associated with disorders, conditions, symptoms, and the like, which may correspond with categorization. Dental grouping 120 may include a predictive classification, where a subject such as a healthy young adult, does not harbor dental factor(s) 108 indicative of obvious current disease or disorder but may include data that indicates a dental grouping 120 with which they may be most closely categorized to. For instance, a family history of osteoporosis, epigenetic events, lifestyle factors, and long-term nutritional impacts, may classify an individual in "enamel loss" dental grouping 120, despite not currently exhibiting any symptomology, but with expectation that calcium and/or phosphorous storage may be compromised in the future. In such an example, nourishment program paradigm may be focused on prevention of enamel loss, wherein nutrition may act as a prophylaxis. Dental parameter 112 may have associated with it an identifier, such as a label, that corresponds to a dental grouping 120. Dental grouping 120 may be stored and/or retrieved from a database.

Continuing in reference to FIG. 1, classifying the dental parameter 112 to a dental grouping 120 may include training a dental classifier using a dental classification machine-learning process and training data including a plurality of data entries of dental parameter data from a subset of categorized subjects. A "dental classifier," as used in this disclosure, is a machine-learning classifier that sorts dental parameter(s) 112 to a dental grouping 120. Dental classifier 124 is generated by a dental classification machine-learning process, which may include any machine-learning algorithm, process, and/or model described herein performed by a machine-learning module, as described in further detail below. Dental classification machine-learning process may generate dental classifier 124 using training data. A classifier may include a machine-learning model, such as a mathematical model, neural net, or program generated by a machine learning algorithm known as a "classification algorithm," as described in further detail below. Dental classifier 124 may sort inputs, such as dental parameter 112, into categories or bins of data, such as classifying the data into dental grouping 120, outputting the bins of data and/or labels associated therewith.

Continuing in reference to FIG. 1, training data for dental classifier 124 may include a set of dental factors 108 as it relates to classes of degradation types, organ and/or tissue types, ability types, and the like. Alternatively or additionally, training data may include a set of dental parameters 112 as it matches to such classes. For instance and without limitation, training data may include ranges of dental factors 108 as they correlate to various degrees of neurodegeneration as it relates to neuropathic pain, chronic pain, acute pain, and the like, wherein the varying degrees of pain may be enumerated by dental parameter 112. Such training data may include dental factors 108 (and/or dental parameters 112) as it relates to dental grouping 120 for subsets of a plurality of subjects, segmented according to subject characteristics such as smoking, alcohol consumption, exercise, dietary patterns, nutritional deficiency, age, sex, ethnicity, and the like. Training data may be used by classification machine-learning process to train dental classifier 124 to derive relationships present in the data that may result in a machine-learning model that automatedly classifies a subject to a dental grouping 120 as a function of their dental parameter(s) 112. Training data may originate from any source described herein, for instance retrieved from a database, retrieved via a web browser and the Internet, peer-reviewed research repository, clinical data, subject input data, wearable device, physiological sensor, medical history data, and the like.

Continuing in reference to FIG. 1, dental classifier 124 may be configured to output at least a datum that labels or otherwise identifies a set of data that are clustered together, found to be close, relate to one another via a metric, scoring, probability, and the like, as described below. Machine-learning module, as described in further detail below, may generate a classifier using a classification algorithm, defined as a process whereby computing device and/or any module and/or component operating thereon derives a classifier from training data. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, a dental parameter 112 training data classifier may classify elements of training data to elements that characterizes a sub-population, including subset of dental factor 108 such as gene expression patterns and epigenetic markers as it relates to a variety of degradation types and/or other analyzed items and/or phenomena for which a subset of training data may be selected.

Continuing in reference to FIG. 1, classifying dental parameter 112 to dental grouping 120 may include classifying the dental parameter 112 to the dental grouping 120 using the dental classifier 124. Classification using dental classifier 124 may include identifying which set of categories (dental grouping 120) an observation (dental parameter 112) belongs. Classification may include clustering based on pattern recognition, wherein the presence of dental factors 108, such as genetic indicators, symptoms, and the like, identified in dental parameter 112 relate to a particular dental grouping 120. Such classification methods may include binary classification, where the dental parameter 112 is simply matched to each existing dental grouping 120 and sorted into a category based on a "yes"/"no" match. Classification done in such a manner may include weighting, scoring, or otherwise assigning a numerical value to elements in dental parameter 112 as it relates to each pain disorder type and assign a subject to a dental grouping 120 that results in the highest score. Such a score may represent a "likelihood", probability, or other statistical evaluation that relates to the classification into dental grouping 120.

Continuing in reference to FIG. 1, computing device 104 may assign the dental grouping 120 as a function of the classifying. Classifying the dental parameter 112 (input) to a dental grouping 120 (output) may include assigning the dental grouping 120 as a function of the dental classifier 124 generated by the dental classification machine-learning process. Training data for dental classifier 124 may include sets of dental parameters and/or dental factors 108, as described above, correlated to dental grouping according to trends observed in the data for subsets of subjects. Subsets of subjects may include subjects belonging to a 'diagnosed cohort' that exhibits similar dental disorder characteristics. Such a set of training data may include dental factors 108 of the cohort, accounting for similar age, sex, and the like. This way, classifier may be trained to relate dental factors 108 in the subject as it would classify the subject to the same (or different) dental grouping 120. Such training data may be used to learn how to categorize a subject's dental parameter 112 to dental grouping(s) depending on trends in the data. In this way, dental classifier 124 may also generate new dental groupings depending on how well a subject may "fit" within a particular classification. For instance, if a particular pattern of subject data does not correlate well to categorizations observed from training data, classifier may have identified a novel grouping of pain disorder, manifestation of symptoms, and the like.

Continuing in reference to FIG. 1, classifying may include classifying the dental parameter 112 to a nutrition-linked dental grouping. A "nutrition-linked dental grouping," as used in this disclosure, is a disorder categorization that indicates a grouping which is sensitive to nutritional modification. Nutrition-linked dental grouping may include a category of current disorders that are not averse to nutritional modification, in that they may be addressed at least in part by varying nutrition levels in the subject. A nutrition-linked dental grouping may include for instance and without limitation a disorder characterized by pain due to enamel hypoplasia, indicative of a vitamin A deficiency, which may lead to impaired epithelial tissue and tooth development, where vitamin A supplementation may "cure" the deficiency where the disorder categorization may be changed with sufficient, sustained nutrient supplementation. Such classification may include identifying biomarkers or any dental factor 108 present in dental parameter 112 which are resistant to nutritional changes and identifying which can be addressed with nutritional modification, altering dietary habits, nutrient supplementation, and the like.

Continuing in reference to FIG. 1, nutrition-linked dental grouping may include identifying relationships between dental parameter 112 and dental grouping which may have nutrition and/or nutrient metabolites as causative factors. In non-limiting illustrative examples, elevated pyroglutamate may be indicative of glutathione depletion, which may result in the manifestation of symptoms. Glutathione depletion may be indicative of chronic protein deficiency in the diet, particularly essential amino acids, as well as increased oxidative stress. In further non-limiting illustrative examples, elevated xanthurenic acid may be indicative of vitamin B6 insufficiency, which can manifest as pain symptomology in subjects, such as angular cheilosis and periodontal diseases. Combination vitamin D and calcium deficiency may cause hypo-mineralization, delayed tooth eruption, the absence of lamina dura, and abnormal alveolar bone patterns. Such correlations are non-limiting examples that may be identified in training data of dental factors 108 as they may relate to symptoms that would classify a subject to a nutrition-linked dental grouping, which may be readily ameliorated, or even cured, with proper nutritional guidance.

Continuing in reference to FIG. 1, classifying may include classifying the dental parameter 112 to a nutrition-linked dental disorder prevention grouping. A "nutrition-linked dental disorder prevention grouping," as used in this disclosure, is a dental disorder categorization for which nutrients may act as a preventative measure. Nutrition-linked dental disorder prevention grouping may include a category which will occur, or is imminent, according to at least a dental parameter 112 of the subject which may be prevented or ameliorated from nutritional modification. A nutrition-linked dental disorder prevention grouping may include a risk for developing dental disorders from acrolein build-up in the future, where the risk may be reduced from nutritional intervention. Classification to such a category may include identifying biomarkers, or any dental factor 108, present in dental parameter 112 which may be modified, over time, with sustained, chronic nutrient manipulation. In this way, dental classifier 124 may identify groupings which are not imminent threats in healthy individuals but may represent sources of pain and/or discomfort in the future which may be avoided with nutritional guidance.

Continuing in reference to FIG. 1, computing device 104 is configured to generate, using the dental parameter 112, an alimentary model. An "alimentary model," as used in this disclosure, is a machine-learning model which may accept a dental parameter 112 input and generate an output of a plurality of alimentary elements according to relationships derived from training data which relate effects of alimentary levels on dental parameters and/or dental groupings. An "alimentary level," as used in this disclosure, is an amount of a nutrient. A "nutrient," as used in this disclosure, is any biologically active compound whose consumption is intended for addressing and/or preventing dental disorder. An "alimentary element," as used in this disclosure, is an item that includes a nutrient intended to be used and/or consumed by subject. Alimentary element 144 may include meals (e.g. chicken parmesan with Greek salad and iced tea), food items (e.g. French fries), grocery items (e.g. broccoli), health supplements (e.g. whey protein), beverages (e.g. orange juice), among other edibles and consumables. Alimentary element 144 may be "personalized" in that alimentary elements are curated in a guided manner according to dental groupings, dental parameter 112, dental factors 108, subject-designated symptoms, food allergies and/or intolerances, subject preferences, or the like, and may contain specific ingredients and/or ingredient combinations not commercially available. Alimentary element 144 may include nutrients such as supplementary use of oral digestive enzymes and/or probiotics which may also have merit as dental nutritional measures. Alimentary elements 144 may include micronutrients such as vitamins, minerals, trace elements, electrolytes, such as selenium, folic acid, vitamin B12, vitamin D, bicarbonate, calcium, and the like. Alimentary elements may include phytonutrients and plant-based macromolecules such as chlorophyll, antioxidants such as the carotenoids (α-carotene, β-carotene, lycopene, lutein, cryptoxanthin), and the like. Alimentary element 144 may contain biologically active compounds that are not typically considered as part of recommended daily nutrients, nor are they intended to provide appreciable amounts of calories, such as phytonutrients, nutraceuticals, antioxidants, and the like; for instance and without limitation, allium and bioactive ingredients present in cruciferous vegetables such as broccoli sprouts, which are known sources of antioxidants such as sulforaphane. Alimentary elements 144 may include a specific dietary category, such as a "ketogenic diet", "low glycemic index diet", "Paleo diet", among others.

Continuing in reference to FIG. 1, generating the alimentary model 132 may include training the alimentary model 132 using training data including a plurality of data entries correlating the plurality of alimentary levels to respective effects on dental parameters and/or dental groupings, and generating the alimentary model 132 as a function of the training. Alimentary model 132 may include any machine-learning algorithm, model, and/or process as performed by a machine-learning module described in further detail below. Training data may include nutrient levels correlated to addressing dental parameter categories. For instance, training data may include nutrient levels, including alimentary element properties such as the pH of beverages, beverage volumes, beverage temperatures, among other physical and chemical properties, correlated to tooth color, enamel porosity, tooth decay, and the like. For instance, an alimentary model 132 may include a "coffee drinker's model", "tea drinker's model", "orange juice drinker's model", and the like, wherein the model relates the consumption of an alimentary element (and the constituent nutrients), including physicochemical properties, to the effect on dental physiology (dental parameter). This may be performed for each diet type, alimentary element type, restaurant type, cuisine type, nutrient category (such as earth alkali metals, transition metals, water-soluble vitamins, fat-soluble vitamins, amino acids, and the like), and individual nutrient (calcium, vitamin A, phosphorous, L-arginine, fluoride, and the like). In this way, alimentary model 132 may include a variety of individual equations, formulas, functions, and the like, derived from relationships observed in the training data for each alimentary element—dental parameter correlation. Persons skilled in the art, upon the benefit of reviewing this disclosure in its entirety, may appreciate the large degree of relationships that may emerge from alimentary model 132, and how the model may be guided based on subject-specific alimentary element preferences, dietary preferences, and/or dental parameter(s) 112, especially according to a subject's goals.

Continuing in reference to FIG. 1, training data for alimentary model 132 may originate from a database, such as a key relational database, NOSQL database, and the like, as described in further detail below. Training data may include a repository of menu items, grocery items, recipes, individual ingredients, among other alimentary elements, linked to their constituent nutrient content. Such training data may include data for nutritional data that is not readily available as nutritional facts, for instance for nutraceuticals, bioactive ingredients, antioxidants, among other biologically active compounds, which are not intended to provide appreciable number of calories, where the data may originate from a guided query using a web browser and the Internet, as input from the subject or a secondary individual such as a dietician, physician, or the like. Training data may include a plurality of dental parameters 112, which may be organized according to classification of a plurality of subjects. For instance and without limitation, such training data may be categorized by a classifier and/or classification machine-learning process, as described in further detail below. Training data may include dental parameters 112 classified by dental disorder, symmetry of teeth, tooth color, gum health, microbiome, or the like, where the subsets of training data may be linked to values describing nutritional levels such as nutrient deficiencies, nutrient surplus, and the like, as it relates to each subject's dental parameter 112. Training data may originate from a second computing device, such as a "smartphone", tablet computer, internet-of-things (IoT) device, or the like, which may communicate with system 100 as described above, and provide raw data elements as the plurality of subject encounters them. In non-limiting illustrative examples, training data may include alimentary elements and their associated nutrients logged as raw training data, stored and/or retrieved from a database, as the user locates the items, such as visiting a restaurant, shopping at a grocery store, save a recipe file from an online source, where the subject encountering the elements has associated dental parameter(s) 112. In such an instance, alimentary model 132 may be trained to identify which alimentary elements subjects with particle dental parameters are consuming, which dental hygiene products they may be using, among other identified relationships. Training data may originate from an online research repository, as described above.

Continuing in reference to FIG. 1, alimentary model 132 generating alimentary level 140 may include generating a nutritional metric. Alimentary level 140 may include a plurality of nutritional metrics which signify, for instance significant nutrient values identified for how the subject's dental parameter(s) 112 relate to a dental disorder, disease, and/or condition. A "nutritional metric," as used in this disclosure, is a quantification of a nutrient, or combination of nutrients, which hold significance to how a dental parameter of the subject the classifies to a dental grouping 120. Nutritional metric may include a minimal nutrient level, below which significant health concerns may exist. Nutritional metric may include a current nutrient amount in the subject, to which the current nutritional status of the subject may classify the subject to a particular dental grouping 120. Nutritional metric may include a numerical value, or plurality of numerical values such as a function, describing averages, medians, standard deviations, variances, and the like, of a nutrient amount or combination of nutrients as it relates to subjects of a particular dental parameter 112 and/or dental grouping 120. Nutritional metric may include a plurality of numerical values describing a variety of mathematical evaluations of nutrient amounts in healthy individuals. Nutritional metric may include a maximal acceptable nutrient level, above which may indicate health concerns, such as leeching of secondary nutrients from the subject (for instance elevated zinc may decrease copper). Nutritional metric may include qualitative values such as binary values, Boolean values such as "true"/"false", "yes"/"no", and the like. Nutritional metric may include quantitative values such as numerical values, mathematical expressions, formulas, equations, functions consisting of a plurality of numerical values according to a correlation or other mathematical relationship. In non-limiting exemplary embodiments, generating a plurality of nutritional metrics may include 1) a minimal acceptable nutrient amount for a subject, 2) a current nutrient amount in a subject, 3) a mean±SD for the nutrient in healthy subjects and/or subjects in a target grouping, and 4) a maximal nutrient amount appropriate for subject. In this way, an alimentary level 140 may be established for subject that may establish and maintain nutritional homeostasis for improving dental conditions by keeping the subject above a custom minimal nutrient amount and below a custom maximal nutrient amount according to the current nutrient amount and how that current amount compares to a cohort of target subjects.

Continuing in reference to FIG. 1, generating the alimentary model 132 includes determining a respective effect of each alimentary level of the plurality of alimentary levels on the dental parameter 112 and generating the alimentary model 132 as a function of the respective effect 136 of the plurality of alimentary levels 140. A "respective effect," as used in this disclosure, is a change, consequence, and/or result in at least a dental factor 108, dental parameter 112, and/or dental grouping 120 in a subject according to alimentary level 140. A respective effect 140 of an alimentary level 140 may be "no effect", "negligible effect", and/or "no calculated effect". Determining respective effect 140 of alimentary level 140 may include determining how a dental factor 108 may change, such as an increase/decrease according to a particular amount of nutrient. For instance and without limitation, such a determination may include calculating the effect of chronic, sustained nutrient amounts in a diet for weeks and/or months on epigenetic factors, blood serum levels of dental factors 108, mouth pain symptoms, and the like. Determining respective effect 140 may allow determination of what is an acceptable minimal nutrient amount, maximal nutrient amount, the effect current nutrient levels is having on dental parameter(s) 112, among other respective effects 140 on alimentary levels 136.

Continuing in reference to FIG. 1, determining a respective effect 140 of each alimentary level 140 of the plurality of alimentary levels 136 may include retrieving the respective effect 140 of each alimentary level 140 on the dental parameter 112 as a function of at least the dental factor 108. Computing device 104 may search for a nutrient effect using each dental factor 108, and/or combination thereof, to locate and retrieve effects correlated to nutrients targeting a dental factor 108. Retrieving an effect of a nutrient may include retrieving a hypothesis about the outcome for a subject after consuming a nutrient amount and/or amount of a combination of nutrients. Such a hypothesis may include an equation, function, among other mathematical forms, for instance derived from empirical relationships between a nutrient and the physiological integrity of an organ, biological system, dental biomarker, and the like. Retrieving an effect may include retrieving from a database, a research repository, or the like. Retrieving an effect may include, for instance, searching using the dental factor 108, a web browser and the Internet, for a plurality of respective effects that nutrients may have to potentially identify a nutritional requirement of the subject that is not being met which may explain the dental factor 108. Retrieving an effect may include searching using the dental grouping 120 for an effect of a nutrient on the type of dental disease. In some embodiments, retrieving an effect may include calculating at least an effect, for instance by deriving a function from training data using a machine-learning algorithm.

Continuing in reference to FIG. 1, in non-limiting illustrative examples, determining respective effect 140 of alimentary level 140 may include calculating if a change in dental grouping 120 may arise from adding and/or removing a nutrient from a subject's diet. For instance and without limitation, changing a dental grouping 120 from "periodontitis" to "gingivitis" to progressing toward "dental parameter>60" with increasing dietary vitamin A, vitamin B, vitamin C, vitamin D, calcium and phosphorous, increasing arginine, and reduction of acrolein by introducing alimentary elements a subject may not currently consume, such as tree nuts, seeds, green leafy vegetables, and the like, while reducing high-temperature use of vegetable oils, cooked animal products, and potentially adding particular dietary supplements. Calculating an effect of a nutrient may include retrieving an empirical equation that describes relationships between a nutrient and dental factor 108, test results, dental parameter 112, and the like. Calculating an effect of a nutrient may include deriving an algorithm, function, or the like, for instance using a machine-learning process and/or model. Calculating such an effect using machine-learning may include training data that includes a plurality of nutrients as it relates to effects on dental groupings 124, dental factors 108, and the like.

Continuing in reference to FIG. 1, determining a respective effect 140 of each alimentary level 140 may include generating a machine-learning model. Training data may include nutrient amounts correlated to their effect on the human body. For instance and without limitation, supplementation of amounts of fat-soluble vitamins, water-soluble vitamins, trace elements, minerals, electrolytes, among other nutrient categories in the diet may be correlated to renal function, liver function, bone mineral density, tooth decay, enamel integrity, and the like. Such training data may originate from a database, research repository, clinical data, physician, plurality of subjects, or any other source described herein. Computing device 104 may generate a machine-learning model with such training data to derive an equation and/or function which describes relationships observed in the training data, for instance that a minimal amount of a vitamin is necessary, but that its effect is nullified if a second vitamin or mineral is not above a particular level. Computing device 104 may then automatedly derive a respective effect for each nutrient, wherein the effect may become increasingly defined by parameters relating to the type and number of dental parameter(s) 112 of the subject. The effect may also be related to an equation wherein, the magnitude of effect may be determined for all amounts of the nutrient. In this way, a particular nutrient amount may be calculated based on the magnitude of effect desired, where the amount can be derived for a plurality of subjects with different dental parameter 112 inputs.

Continuing in reference to FIG. 1, computing device 104 is configured to identify, using the alimentary model 132, a plurality of alimentary elements 144. Identifying a plurality of alimentary elements 144 may include identifying alimentary elements 144 supporting at least an alimentary level 140 as a function of the respective effect 140, wherein the alimentary level 140 includes a nutrient amount intended to address the dental parameter 112. Alimentary level 140 may include a therapeutic amount of a nutrient intended to address dental parameter 112. Alimentary element 144 may include mass amounts of a vitamin, mineral, macronutrient (carbohydrate, protein, fat), a numerical value of calories, amounts of phytonutrients, antioxidants, probiotics, nutraceuticals, bioactive ingredients, and the like. Alimentary element 144 may include the calculated amount of a nutrient, or combination of nutrients, a subject should consume according to a plurality of nutritional metrics, such as the subject's current nutrient amount, the minimal and maximal acceptable amounts, and the nutrient amount in healthy individuals. Alimentary element 144 may include the alimentary level 140 the subject is intended to consume in a meal, the day, week, and the like. Alimentary element 144 may include the nutrient amount the subject is expected to have, for instance in the blood, after consuming a particular amount in the diet. In such an instance, Alimentary element 144 may include alimentary level 140 that is modified by a weighting factor that is determined according to a subject's pharmacokinetics. Such a weighting factor may include an empirical formula that weights each nutrient amount consumed according to the nutrient source (organic vs inorganic), the type of alimentary element 144, the metabolism and absorption of the nutrient, to the concentration that ends up in a tissue and/or fluid in the subject.

Continuing in reference to FIG. 1, identifying the plurality of alimentary elements 144 may include calculating the alimentary level 140 the subject may receive from an alimentary element 144. Calculating may include generating a nutrition machine-learning model using training data, wherein training data may include a plurality of data entries correlating the pharmacokinetics of a plurality of nutrients found in a plurality of alimentary elements to the achievable alimentary levels in the subject according to metabolism and adsorption by a plurality of subjects. Such training data may be used to train the model to identify the serving size of the alimentary element 144 as a function of the target alimentary level 140 and what nutrient level is expected to be achieved from each alimentary element. Training data may include nutrient amounts found in the blood after consumption of each alimentary element, where nutrient amounts range from [x, y], where x is a minimal expected nutrient amount and y is a maximal expected nutrient amount, and each discrete amount in the range of nutrient values is correlated to a feasible serving size of alimentary element. For instance, vitamin A (retinol) from a variety of alimentary element 144 sources (egg yolks, fish, vegetables, fruits, and the like) correlated to how much of the nutrient reaches the gums, and what the respective effect of that much of the nutrient has on the dental parameter 112. Training data may include nutrient combinations from peer-reviewed studies correlated to enamel care, tooth color, and/or oral cancer, for instance vitamin D, calcium, phosphorous, omega-3 polyunsaturated fatty acids, glucosamine, arginine, chondroitin, and various salts of each in combination which may restore enamel, dentin, gingiva, cementum, pulp, ligaments, and/or nerves of teeth in certain cohorts of subjects. In such an example, each nutrient may have a respective effect 140 according to a plurality of alimentary levels 136, wherein the levels may be correlated to nutrient amounts from alimentary elements 144 that may dictate which alimentary elements 144 may be identified for the subject. Training data may include identified nutrient deficiencies in cohorts of subjects that may or may not consume particular alimentary elements 144 for identification. Training data may correspondingly include nutrient surpluses, where overeating of particular alimentary elements 144, such as food items high in particular sugars results in accelerated tooth decay, microbiome imbalance, saliva flow rates, viscosity, and the like. Training data may originate from any source described herein, for instance and without limitation, from a physician, via subject input from a plurality of subjects, web browser and the Internet, a database, as described in further detail below, research repository, wearable device, physiological sensor, and the like.

Continuing in reference to FIG. 1, identifying a plurality of alimentary elements may include calculating alimentary levels 136, for instance, by retrieving a default amount from a database. Computing device 104 may retrieve standard nutrient amounts, such as from a standard 2,000 calorie diet, and alter the amount according to a numerical scale associated with dental factors 108 in the dental parameter 112. Such a calculation may include a mathematical expression using operations such as subtraction, addition, multiplication, and the like, for instance an equation that assigns a variable to the subject's dental factors 108 enumerated in the dental parameter 112 and retrieve a start value of a vitamin and alter the amount using the mathematical expression. Alternatively or additionally, such a calculation may involve deriving a loss function, vector analysis, linear algebra, system of questions, among other mathematical heuristics, depending on the granularity of the process. Deriving such a process for calculating nutrient amounts may include machine-learning, as described herein. Alimentary level 140 may include threshold values, or ranges of values, for instance and without limitation, between 80-120 mg vitamin C per 24 hours, wherein the range changes as a function of dental parameter 112 and/or dental grouping 120. Alimentary level 140 may be calculated as heat maps (or similar mathematical arrangements), for instance using banding, where each datum of dental parameter 112 elicits a particular range of a particular alimentary level 140 or set of nutrient amounts. In non-limiting illustrative examples, such a calculation may include querying for and retrieving a standard amount of water-soluble vitamins for a healthy adult, for instance as described below in Table 1:

| Nutrient | Amount |
| --- | --- |
| Vitamin C | 60 mg/day |
| Thiamin (B1) | 0.5 mg/1,000 kcal; 1.0 mg/day |
| Riboflavin (B2) | 0.6 mg/1,000 kcal; 1.2 mg/day |
| Niacin (B3) | 6.6 NE/1,000 kcal; 13 ND/day |
| Vitamin B6 | 0.02 mg/ 1g protein; 2.2 mg/day |
| VitaminB12 | 3 µg /day |
| Folic Acid | 400 µg /day |
| Table 1 | |

Continuing in reference to FIG. 1, in reference to Table 1 above, wherein NE is niacin equivalent (1 mg niacin, or 60 mg tryptophan), mg (milligram), kcal (1000 kcal=1 Calorie), and µg (microgram). Computing device 104 may store and/or retrieve the above standard alimentary levels 136, for instance in a database. The amounts may be re-calculated and converted according to a subject's dental parameter 112. For instance, these amounts may relate to an average BMI, healthy adult male, for any range of calories, but may be adjusted according to unique subject-specific dental factors 108 and rates of pharmacokinetics. In non-limiting illustrative examples, a geriatric woman who is on a 1,400 Calorie/day diet, with onset of osteoporosis and need for dentures may prompt calculation of alimentary levels 136 according to identified risk factors and the above alimentary levels 136 may be recalculated, where some amounts may increase, some may decrease, and some may remain constant.

Continuing in reference to FIG. 1, calculating alimentary levels 136 may include deriving a weighting factor to adjust, or otherwise re-calculate, an amount. Weighting factor may be determined by computing device 104, for instance, by querying for vitamin amounts according to data inputs identified in the dental parameter 112. For instance in non-limiting illustrative examples, if dental factor 108 indicates the presence of elevated quinolinic acid, indicative of as a downstream metabolite of the kynurenine pathway, which metabolizes tryptophan. Increased levels of quinolinic acid may act as a neurotoxin, and signal a vitamin B3 deficiency, manifesting as tooth pain, angular cheilosis, and/or periodontal diseases in subjects. Respective effect 140 may be found in alimentary levels 136 relating to the slowing of quinolinic acid damage, specifically in supplementing the diet with kynurenic acid supplements, specific foods rich in antioxidants and phenols such as catechin hydrate, curcumin, epigallocatechin gallate, such as legumes, nuts, seaweed, avocados, cranberries, teas such as green tea, white tea, oolong tea, and the like, whereas it may be inversely associated with consumption of alcohol, certain animal products such as red meat and/or processed meat, and/or nicotine consumption. Although, alimentary model 132 may identify that vitamins found in alimentary elements 144 from organic sources may be superior from nonorganic sources, such as from commercially available supplements, from a bioavailability standpoint. Additionally, per-subject pharmacokinetics, rates of metabolism and/or adsorption of nutrients may differ subject-to-subject, which may negate the effectiveness of proscribing particular diet types and alimentary levels 136 to subjects, for instance where foods high in tryptophan may exacerbate quinolinic acid build-up, but vitamin B3 supplementation may not. In such an instance, computing device 104 may account for such details using machine-learning to derive more specific alimentary level 140 calculations and to more accurately identify the alimentary element 144 amounts by which to increase/decrease nutrients. Therefore, computing device 104 may derive weighting factors to account for particular gene expression patterns, organic vs non-organic sources, pharmacokinetics, type of pain experience, and the like.

Continuing in reference to FIG. 1, in non-limiting illustrative examples, computing device 104 may use a machine-learning process to perform a machine-learning algorithm to derive per-subject pharmacokinetics, for instance of vitamin B6. Vitamin B6 deficiency may be indicative by elevated xanthurenic acid which may be observed in at least 1-in-6 subjects who experience chronic pain. The machine-learning algorithm may accept an input of numerical values including the total amount of protein consumed (in grams), total amount of vitamin B6 consumed (in mg) per day in a diet, and serum levels of the vitamin B6 vitamer, pyridoxal-5-phosphate, over the course of a month, and derive the rates of metabolism, or how 'well' the subject is obtaining the vitamin from alimentary elements 144 and adsorbing vitamin B6. In other words, the algorithm may derive a function such as using linear regression, vector quantization, least squares, among other algorithms, that describes the pharmacokinetics for that particular subject regarding what amount of vitamin B6 consumed, per amount of dietary protein, results in what corresponding amount of bioactive vitamin compound, as measured by the blood vitamer from a biological extraction. Such a function, derived from machine-learning, may then be used by computing device 104 with an input of the dental parameter 112, which enumerates dental factors 108, to calculate an output which is a more accurate, customized, per-subject alimentary level 140 of vitamin B6, and potentially protein. Persons skilled in the art, upon benefit of this disclosure in its entirety, may appreciate that this process may be repeated for the full spectrum of nutrients, both required as part of a diet and not required as part of a diet, to control for specific metabolic differences in a population for addressing dental factors 108, dental parameters 112, dental groupings 120.

Continuing in reference to FIG. 1, additionally, in non-limiting illustrative examples, computing device 104 may relate the concentrations of the metabolic products related to vitamins (e.g. vitamers), minerals, phytonutrients, probiotics, antioxidative compounds, biologically activity ingredients, prodrugs, and the like, to their effective concentrations in tissues related to various dental groupings 120. For instance, computing device 104 may additionally search and retrieve data that relates the blood levels of the vitamin B6 vitamer, pyridoxal-5-phosphate, to the effective concentrations of vitamin B6 in the mouth epithelial, gums, and/or teeth. Computing device 104 may store and/or retrieve values in a "look-up table", or graph a relationship as a mathematical function, among other ways of representing a data structure that relates the data identified in the search. Alternatively or additionally, computing device 104 may derive a function, for instance using machine-learning, which correlates the concentration of a compound in a particular biological extraction, such as saliva and/or blood, to varying amounts in tissues such as tongue, teeth, gums, peripheral nervous system, and the like. This may prove helpful in calculating alimentary levels 136 as a function of subject consumption to specific target nutritional quantities within a particular organ/tissue according to the input data in the dental parameter 112 for identifying alimentary elements 144.

Continuing in reference to FIG. 1, identifying the plurality of alimentary elements 144 may include retrieving the plurality of alimentary elements 144 as a function of the dental grouping 120. Identifying the plurality of alimentary elements 144 may include retrieving alimentary elements that include at least a nutrient amount of the plurality of alimentary levels 136 intended to cure, ameliorate, or otherwise alter dental grouping 120. Computing device 104 may accept an input of at least a dental grouping 120 and generate an output of alimentary elements 144 by searching a database for alimentary elements according to the dental grouping 120. Computing device 104 may accept an input of alimentary level 140 associated with dental grouping 120 and may search using a web browser and the Internet for alimentary elements 144 according to the alimentary level 140 and the dental grouping it is meant to address.

Continuing in reference to FIG. 1, identifying the plurality of alimentary elements 144 may include identifying the plurality of alimentary elements 144 as a function of the at least an alimentary level 140. Computing device 104 may identify the plurality of alimentary elements 144 by using alimentary level 140 as an input and generating combinations, lists, or other aggregates of alimentary elements 144 necessary to achieve alimentary level 140. For instance, computing device 104 may use a template alimentary level 140 of '200 mg vitamin C' and build a catalogue of alimentary elements 144 until the 200 mg vitamin C value is obtained. Computing device 104 may perform this task by querying for food items, for instance from a menu, grocery list, or the like, retrieving the vitamin C content, and subtracting the value from the alimentary level 140. In non-limiting illustrative examples, computing device 104 may identify orange juice (90 mg vitamin C/serving; 200 mg−90 mg=110 mg) for breakfast, Brussel sprouts (50 mg vitamin C/serving; 110 mg−50 mg=60 mg) for lunch, and baked potato (20 mg vitamin C/serving) and spicy lentil curry (40 mg vitamin C/serving; 60 mg−(20 mg+40 mg)=0 mg) for dinner. In such an example, computing device 104 may compare such alimentary elements against a set of instructions such as food preferences, allergies, restrictions, and the like, provided by a physician, medical history, subject input, among other sources, and subtract each identified alimentary element 144 from alimentary level 140 until a combination of alimentary elements 144 that represents a solution is identified. Once a solution is found, computing device 104 may generate a file of alimentary elements 144 and store in a database, as described in further detail below. In this way, computing device 104 may generate customized meals, health shakes, recipes, and the like, according to alimentary levels 136, where computing device 104 may retrieve alimentary elements 144 from the database according to subjects with matching alimentary levels 136.

Continuing in reference to FIG. 1, identifying the plurality of alimentary elements 144 may include retrieving the alimentary elements 144 as a function of the dental grouping 120. Identifying alimentary element 144 according to dental grouping 120 may include querying, for instance using a web browser and the Internet, for foods, supplements, bioactive ingredients, and the like, which are correlated with a particular dental grouping 120. For instance and without limitation, computing device 104 may organize a search for foods intended for "improving tooth color", wherein an entire diet may be crafted around adding and/or eliminating alimentary elements 144 intending to improve tooth color. In such an example, the alimentary elements 144 are outputs generated from an input search criteria of "improving tooth color". The output elements become "personalized" as they are arranged into daily, weekly, monthly, and the like, individual meals and/or meal schedule according to a subject's particular calculated alimentary levels 136 and personal dental hygiene patterns. The dental grouping 120 may serve as a filtering step, wherein a search is guided by the dental parameter 112 as it was classified to a dental grouping 120 where particular alimentary elements may be included and/or avoided.

Continuing in reference to FIG. 1, computing device 104 may be configured to develop, using plurality of alimentary elements, a hygienic model. A "hygienic model," as used in this disclosure, is a model that may accept a plurality of alimentary elements as inputs and generate at least a hygienic pattern as a function of the alimentary elements and output an ordering of the plurality of alimentary elements and the at least a hygienic pattern. Hygienic model 148 may include any machine-learning model, algorithm, and/or process as performed by a machine-learning module described in further detail below. A "hygienic pattern," as used in this disclosure, is a scheduled use of a dental hygiene pattern in a repeated and predictable manner. Hygienic pattern 152 may include actions such as brushing teeth, flossing, using mouthwash, consuming a prebiotic and/or probiotic, among other oral, dental, and/or health care modalities. Hygienic pattern 152 may include products and active ingredients for oral, dental, and/or health care such as ingredients for whitening, sensitive teeth and/or gums, removing plaque, calculus, tartar, and the like, including hydrogen peroxide, carbamide, potassium nitrate, stannous fluoride, strontium chloride, methyl salicylate, essential oils and/or plant-derived ingredients such as menthol, limonene, eucalyptol, thymol, and the like. Hygienic pattern 152 may include rituals, methods, and/or tasks associated with oral surgery and orthodontics such as wisdom tooth removal and use of a water pick, cleaning after eating with braces, using a retainer, dentures, and the like. Hygienic pattern 152 may include a frequency and a magnitude associated with product use.

Continuing in reference to FIG. 1, in non-limiting illustrative examples, hygienic pattern may include fluorinated drinking water immediately after eating to stimulate saliva and prevent cavities, followed by flossing within 30 min of eating, and brushing teeth at least 1 hour after a meal, and no more than within 1 hour leading up to eating a meal, and no less than twice daily. Such a hygienic pattern may be optimally arranged according to the type of alimentary element 144 consumed, for instance if an acidic beverage is consumed such as coffee, fruit juice, or the like, the pattern may be altered. In such an instance, depending on dental parameter 112, the hygienic pattern may include altering the products used, where products higher in ingredients to combat sensitive teeth such as potassium nitrate and strontium chloride are swapped out for products with fluoride to be used immediately after, and hygiene products including whitening active ingredients such as hydrogen peroxide and/or carbamide are used at the end of days with heavy coffee drinking to combat teeth staining.

Continuing in reference to FIG. 1, hygienic model 148 may receive alimentary elements 144 as inputs and may identify dental hygiene products which are congruent with each alimentary element 144, meal, diet, and/or any other arrangement of alimentary elements 144. Alternatively or additionally, computing device 104 may receive nutritional input from subject, and generate a hygienic model according to the nutritional input and the dental parameter 112 (and/or dental grouping 120) of the subject to provide an optimal hygiene pattern for the subject to follow.

Continuing in reference to FIG. 1, "nutritional input," as used in this disclosure, is an amount of a nutrient consumed by a subject. Nutritional input may be received and/or calculated, for instance and without limitation, as described in Ser. No. 16/911,994, filed Jun. 25, 2020, titled "METHODS AND SYSTEMS FOR ADDITIVE MANUFACTURING OF NUTRITIONAL SUPPLEMENT SERVINGS," the entirety of which is incorporated herein by reference. Computing device 104 may receive nutritional input from a subject. Nutritional input, for instance and without limitation, may include alimentary elements that have associated nutrition facts, wherein computing device 104 may calculate, weight, or otherwise modify, the nutritional input from the subject, such as with a weighting factor. This results in accurate, per-subject nutritional input, where each alimentary element 144 consumed may be broken down into its constituent nutrients and what amount of that nutrient was absorbed by the subject. That nutritional input may be used as an input to hygiene model 148 to determine hygienic pattern.

Continuing in reference to FIG. 1, computing device is configured for developing the hygienic model 148 as a function of the hygienic patterns 152 and the plurality of alimentary elements 144. Hygienic model 148 may be generated by a machine-learning process and training data including a plurality of data entries correlating dental outcomes from dental products to consumption of alimentary elements. Such training data, for instance and without limitation, may correlate levels of teeth whitening from a variety of dental products, where the timing of the product after consuming food items is associated with an efficacy. Such training data may be used to train a machine-learning algorithm such as a linear regression model to determine which products should be used, at what times, and after which alimentary elements. This way, subject may always know which hygiene pattern is best according to their diet. Training data may originate from nutritional input, for instance via a graphical user interface and computing device from a plurality of subjects. Training data may be stored and/or retrieved from a database, as described in further detail below. Training data may originate from a research repository, such as clinical data from a plurality of dentists and orthodontists. A plurality of hygienic patterns may be retrieved from a database, using a web browser and the Internet, or received as input for instance from a dentist, telemedicine platform, and the like.

Continuing in reference to FIG. 1, alternatively or additionally, generating the hygienic model 148 may include generating a linear programming function with the at least the plurality of alimentary elements wherein the linear programming function outputs at least an ordering of a plurality of alimentary elements 144 according to constraints from a plurality of hygienic patterns 152. A "linear programming function," as used in this disclosure, is a mathematical function that may be used by computing device 104 to score each possible combination of alimentary elements 144 and hygienic pattern 152, wherein the objective function may refer to any mathematical optimization (mathematical programming) to select the 'best' element from a set of available alternatives. Selecting the 'best' element from a set of available alternatives may include a combination of alimentary elements 144 which achieves the nutritional level(s) 140 in addressing dental parameter 112 paired with the hygienic pattern 152 which best address dental grouping 120 in a subject. Linear programming function may be simply referred to herein as an "objective function".

Continuing in reference to FIG. 1, an objective function may include performing a greedy algorithm process. A "greedy algorithm" is defined as an algorithm that selects locally optimal choices, which may or may not generate a globally optimal solution. For instance, computing device 104 may select combinations of alimentary elements 144 so that values associated therewith are the best value for each category. For instance, in non-limiting illustrative example, optimization may determine the combination of the most efficacious 'frequency', 'magnitude', 'probiotic product', 'vegetable containing a polyphenol', 'tooth sensitivity product', 'number of times brushing teeth', among other categories to provide a combination that may include several locally optimal solutions but may or may not be globally optimal in combination.

Still referring to FIG. 1, objective function may be formulated as a linear objective function, which computing device 104 may solve using a linear program, such as without limitation, a mixed-integer program. A "linear program," as used in this disclosure, is a program that optimizes a linear objective function, given at least a constraint; a linear program may be referred to without limitation as a "linear optimization" process and/or algorithm. For instance, in non-limiting illustrative examples, a given constraint might be a metabolic disorder of a subject, as indicated by subject preference, and a linear program may use a linear objective function to calculate combinations, considering how these limitations effect combinations. In various embodiments, system 100 may determine a set of instructions towards addressing a subject's dental grouping 120 that maximizes a total dental parameter 112 score subject to a constraint that there are other competing objectives. For instance, if achieving one nutrient amount by selecting from a first alimentary element 144 category may result in needing to select a second alimentary element 144 from a second category, wherein each may compete in improving dental parameter 112 (e.g. adopting two or more diet types simultaneously may not be feasible, a vegan option and a non-vegan option, and the like). A mathematical solver may be implemented to solve for the set of instructions that maximizes scores; mathematical solver may be implemented on computing device 104 and/or another device in system 100, and/or may be implemented on third-party solver.

With continued reference to FIG. 1, objective function may include minimizing a loss function, where a "loss function" is an expression of an output of which a process minimizes to generate an optimal result. For instance, achieving alimentary levels 136 and adhering to a particular hygienic pattern 152 may be set to a nominal value, such as '100', wherein the objective function selects elements in combination that reduce the value to '0', wherein the alimentary levels 136 are '100% achieved'. In such an example, 'maximizing' the optimal result would be selecting the combination of alimentary elements 144 and timing the use of hygiene products that results in achieving alimentary levels 136 while minimizing the difference. As a non-limiting example, computing device 104 may assign variables relating to a set of parameters, which may correspond to pain symptom prevention components, calculate an output of mathematical expression using the variables, and select an objective that produces an output having the lowest size, according to a given definition of "size." Selection of different loss functions may result in identification of different potential combinations as generating minimal outputs, and thus 'maximizing' efficacy of the combination.

Continuing in reference to FIG. 1, computing device 104 is configured to build a dental nourishment program using alimentary model 132; in an embodiment, computing device 104 may build the dental nourishment program using the alimentary model 132 and hygienic model 148. A "dental nourishment program," as used in this disclosure, is a collection of a plurality of alimentary elements 144 and/or at least a hygienic pattern 152 ordering according to schedule for addressing dental disorder and/or disease. Dental nourishment program 156 may be organized into a frequency and/or magnitude. A "frequency," as used in this disclosure, is a number of consumption occurrences associated with a time course, such as daily, weekly, monthly, and the like, of which an alimentary element 144 is intended to be consumed and/or dental hygiene product to be used. Frequency may be determined as a function of the respective effect 140, wherein the frequency of consumption is tailored to provide a sufficient minimal nutrient level over a time. A "magnitude," as used in this disclosure, is a serving size of at least an alimentary element 144 as a function of the respective effect 140. Magnitude may include a duration and/or amount associated with hygiene pattern such as "brushing 4 times daily", "1 min mouthwash rinse", and the like. Identifying the magnitude associated with an alimentary element 144 may include calculating a serving size as a function of the respective effect 140 and alimentary level 140.

Continuing in reference to FIG. 1, dental nourishment program 156 may include gathering, classifying, or otherwise categorizing alimentary element 144 and/or hygienic pattern 152 lists, which incorporates dental grouping 120-specific recommendations. For instance, alimentary elements 144 may be scored with a numerical score scale that associates a meal, beverage, supplement, and the like, with treating gingivitis, reduce enamel decay, and the like. Dental nourishment program 156 may include selecting alimentary elements 144 according to a threshold score, where items above the threshold are selected and arranged into meals. Threshold score may include a daily threshold, wherein alimentary elements 144 are selected each day according to the threshold; and threshold may include a numerical value relating to symptom prevention, a calculated alimentary level 140, among other outputs of system 100 described herein. Determining dental nourishment program 156 may include machine-learning. For instance and without limitation, computing device 104 may be configured to train a machine-learning model to identify a scoring rubric for building the dental nourishment program 156 based on some criteria such as preventing tooth decay, decreasing a pathogenic bacterial species, decreasing and/or increasing concentration of dental factor 108, among other criteria. Dental nourishment program 156 may relate specific dental grouping 120 to specific nutrients of interest and provide alimentary element 144 scheduling frequency and magnitude for each meal. Dental nourishment program 156 may differ from one subject to the next according to the magnitude of the disease outline (dental grouping 120 and dental parameter 112).

Continuing in reference to FIG. 1, generating the dental nourishment program 156 may include receiving a subject preference. A "subject preference," as used in this disclosure, is a subject input that designates a preference related to at least an alimentary element 144. Subject preference may include designations of alimentary elements 144 to avoid and/or include such as particular food groups, condiments, spices, dietary restrictions such as 'no animal products', cuisine type such as 'Mediterranean foods', time of day for eating such as 'fasting before 10 am', and the like. Subject preference may include indications of allergies, food intolerances, and the like, which may represent constraints on curating alimentary elements 144. In this way, computing device 104 may accept an input of subject preference filter, sort, classify, or otherwise modify the data structure of alimentary elements 144 and schedule the alimentary elements 144 into dental nourishment program 156 in a custom, per-subject manner. Computing device 104 may modify the plurality of alimentary elements 144 as a function of the subject preference, for instance by providing recipes with steps omitted, new steps added, or entirely new recipes altogether utilizing the same or different alimentary elements 144. Computing device 104 may modify the plurality of alimentary elements 144 as a function of the subject preference by generating a new file, based on the preference, and storing and/or retrieving the file from a database, as described in further detail below.

Continuing in reference to FIG. 1, generating the dental nourishment program 156 may include generating a linear programming function and/or objective function with a plurality of alimentary elements 144 and/or a plurality of hygienic patterns 152, wherein the linear programming function outputs at least an ordering of alimentary elements 144 and/or hygienic patterns 152 according to constraints from the subject preference. Generating the dental nourishment program 156 may include generating a linear programming function and/or objective function, as described above, including a linear program, loss function, greedy algorithm, among any other suitable mathematical optimization.

Continuing in reference to FIG. 1, generating the dental nourishment program 156 may include generating a dental program classifier using a dental program classification machine-learning process to classify alimentary elements 144 to the plurality of alimentary levels 136, and outputting the plurality of alimentary elements 144 as a function of the dental program classifier. Dental program classifier may include any classifier, as described above, generated by a classification machine-learning process using training data, performed by a machine-learning module as described in further detail below. Training data for dental program classifier may include sets of data entries that include alimentary elements 144 that are correlated to alimentary levels 136 that classifier may be trained to automatedly locate, sort, and output alimentary elements 144 according to calculated alimentary levels 136 for the subject. Such training data may originate via a database, the Internet, research repository, and the like, as described above for training data for other machine-learning processes. Training data may include alimentary elements 144, correlated to nutrition facts, nutrients, medicinal qualities, and the like, which a classifier may be trained to locate relationships that aid in locating alimentary elements 144 specifically for addressing dental grouping 120. Dental program classifier may accept an input of alimentary levels 136 and output a plurality of alimentary elements 144 with associated frequency and magnitude schedule according to relationships between alimentary elements 144, alimentary levels 136, and appropriate hygiene patterns 152. For instance and without limitation, dental program classifier may identify relationships between individual fruits and vegetables, that when more vegetables are selected, certain fruits may not be necessary to schedule within the same timeframe. Such a classification process may determine a function, system of equations, and the like, which can be solved for in determining which alimentary elements 144 are useful toward obtaining the alimentary levels 136, while not missing some lower limits of alimentary levels 136 (trace elements) and not exceeding upper limits for other alimentary levels 136 (calories).

Continuing in reference to FIG. 1, dental nourishment program may include a dental index. A "dental index," as used in this disclosure, is a score that reflects the subject's dental health as a function of what the subject has consumed, in the case of alimentary levels 136 and/or performed, in the case of hygienic model 148 elements. Dental index 160 may reflect the level of subject participation and/or adherence to dental nourishment program 156. Dental index 160 may include a numerical value, metric, parameter, and the like, described by a function, vector, matrix, or any other mathematical arrangement. Dental index 160 may include enumerating a subject's current nourishment as it relates to managing dental factors 108, dental parameter 112, addressing dental grouping 120, and/or symptom prevention. Dental index 160 may include for instance the "smile health", which may include tooth color improvement, gum health improvement, enamel build-up rate, and the like. In non-limiting illustrative embodiments, dental index 160 may reach a threshold which indicates a time to visit a dental professional, get cleaning/check-up, and the like. Dental index 160 may increase with dental visits and adhering to dental nourishment program 156, decrease if >6 mo. since last cleaning, skipping days of program, missing hygienic pattern 152, and the like.

Continuing in reference to FIG. 1, generating the dental nourishment program 156 dental index 160 may include receiving nutritional input from a subject. Adherence to dental nourishment program 156 may be determined from nutritional input, and the alimentary level 140 may be determined from adherence to the dental nourishment program 156. Nutritional input of a subject may include a designation of any alimentary elements 144 subject may have consumed, such as via the client device and graphical user interface. Alimentary elements 144 may have alimentary levels 136 associated therewith, which may be applied to a subject's current dental parameter 112, dental grouping 120, and the like, representing an update to the data as the subject consumes alimentary elements 144. Applying the alimentary levels 136 may include calculating a difference in dental index 160. Applying the alimentary levels 136 may include calculating a change in dental parameter 112, dental grounding 120, dental index 160, and/or incidence of symptoms in the future, as a function of achieving alimentary levels 136.

Continuing in reference to FIG. 1, generating dental index 160 may include generating an indexing model using training data including a plurality of data entries correlating the respective effect of each alimentary element on the dental parameter. An "indexing model", as used in this disclosure, is a machine-learning model that derives a scoring function for assigning dental index 160 according to nutritional input. Indexing model 164 may include any machine-learning algorithm, model, and/or process, described herein, that may be performed by machine-learning module as described in further detail below. Training data for indexing model 164 may originate from a database, retrieved by a web browser and the Internet, received as input via a client device, a plurality of subjects, a physician, peer-reviewed research repository, among any other source described herein. Training data for indexing model 164 may include respective effects 140 of nutrition levels 140 and hygienic patterns 152 correlated to effects on dental factor 108, dental parameter 112, and/or dental grouping 120 so that relationships observed in such training data may be used to derive a mathematical relationship, such as a function, to determine a scoring function for how each consumed alimentary element 144 and/or each hygienic pattern 152 followed may relate to an effect on dental index 160. Indexing model 164 may then use such training data to determine the scoring index, the maximal score, minimal score, and the incrementation by which in increase/decrease dental index 160 according to what subject consumes and how they adhere to hygienic pattern 152—both from dental nourishment program 156 and items and/or products from outside the program.

Continuing in reference to FIG. 1, alternatively or additionally, dental factor machine-learning model 116 may be used to derive numerical scales for providing numerical values to dental parameter 112. Dental factor machine-learning model 116 may "learn" the upper and lower limits to the numerical scale, the increments to providing scoring, and the criteria for increasing and decreasing elements encompassed in the dental parameter 112. Such a scoring function may operate similarly to the indexing model 164 for providing the dental index 160. In doing so, dental factor machine-learning model 116 may derive a theoretical scale for providing an objective value to dental parameter 112, wherein the dental parameter 112 may change as a function of the dental index 160 of the subject.

Continuing in reference to FIG. 1, in non-limiting illustrating examples, falling short of calcium, phosphorous, and B vitamin alimentary levels 136, may have a particular effect on dental index 160 for an individual who has been classified to a certain dental grouping 120. Where, chronically falling short of the alimentary level 140 results in a (−3) score each month but falling within the alimentary level 140 range for those nutrients affords (+1) score for each month; the target amount for the preceding month may dictate the score change for each subsequent month. In such a case, a machine-learning model may derive an algorithm which dictates the amount to increase/decrease dental index 160 for that particular dental grouping 120 according to the alimentary levels 136. In this case, the indexing model 164 may be trained to identify the relationship between alimentary levels 136 and effect on pain reduction to derive an equation that relates scoring criteria to what is consumed. The score is then calculated using the indexing model 164 and nutritional input. Consumption by the subject may include amounts and identities of alimentary elements 144. In this way, computing device 104 may calculate a dental index 160 as a function of a subject's participation in dental nourishment program 156, where dental index 160 is updated with each alimentary element 144 consumed by subject.

Figure 2:
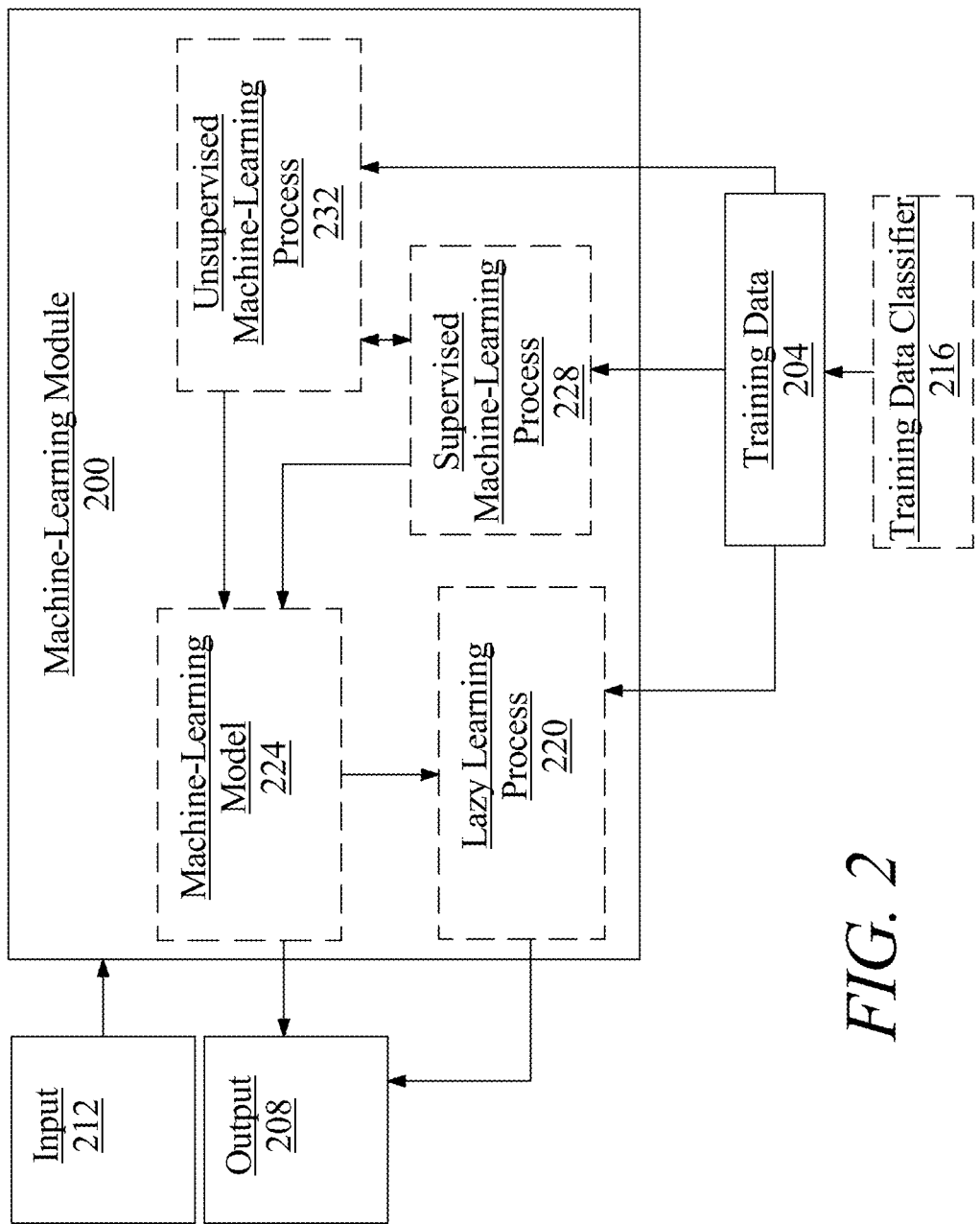
FIG. 2 is a block diagram illustrating an exemplary embodiment of a machine-learning module.

Referring now to FIG. 2, an exemplary embodiment of a machine-learning module 200 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 204 to generate an algorithm that will be performed by a computing device/module to produce outputs 208 given data provided as inputs 212; this is in contrast to a non-machine learning software program where the commands to be executed are determined in advance by a subject and written in a programming language.

Still referring to FIG. 2, "training data," as used herein, is data containing correlations that a machine-learning process may use to model relationships between two or more categories of data elements. For instance, and without limitation, training data 204 may include a plurality of data entries, each entry representing a set of data elements that were recorded, received, and/or generated together; data elements may be correlated by shared existence in a given data entry, by proximity in a given data entry, or the like. Multiple data entries in training data 204 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 204 according to various correlations; correlations may indicate causative and/or predictive links between categories of data elements, which may be modeled as relationships such as mathematical relationships by machine-learning processes as described in further detail below. Training data 204 may be formatted and/or organized by categories of data elements, for instance by associating data elements with one or more descriptors corresponding to categories of data elements. As a non-limiting example, training data 204 may include data entered in standardized forms by persons or processes, such that entry of a given data element in a given field in a form may be mapped to one or more descriptors of categories. Elements in training data 204 may be linked to descriptors of categories by tags, tokens, or other data elements; for instance, and without limitation, training data 204 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 2, training data 204 may include one or more elements that are not categorized; that is, training data 204 may not be formatted or contain descriptors for some elements of data. Machine-learning algorithms and/or other processes may sort training data 204 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 204 to be made applicable for two or more distinct machine-learning algorithms as described in further detail herein. Training data 204 used by machine-learning module 200 may correlate any input data as described in this disclosure to any output data as described in this disclosure.

Further referring to FIG. 2, training data may be filtered, sorted, and/or selected using one or more supervised and/or unsupervised machine-learning processes and/or models as described in further detail herein; such models may include without limitation a training data classifier 216. Training data classifier 216 may include a "classifier," which as used in this disclosure is a machine-learning model as defined herein, such as a mathematical model, neural net, or program generated by a machine learning algorithm known as a "classification algorithm," as described in further detail herein, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 200 may generate a classifier using a classification algorithm, defined as a process whereby a computing device and/or any module and/or component operating thereon derives a classifier from training data 204. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 216 may classify elements of training data to elements that characterizes a sub-population, such as a subset of dental factors 108 (as it relates to dental parameter 112) and/or other analyzed items and/or phenomena for which a subset of training data may be selected.

Still referring to FIG. 2, machine-learning module 200 may be configured to perform a lazy-learning process 220 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of predictions may be performed to cover an initial heuristic and/or "first guess" at an output and/or relationship. As a non-limiting example, an initial heuristic may include a ranking of associations between inputs and elements of training data 204. Heuristic may include selecting some number of highest-ranking associations and/or training data 204 elements, such as classifying dental factor 108 elements to dental parameter 112 elements and assigning a value as a function of some ranking association between elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail herein.

Alternatively or additionally, and with continued reference to FIG. 2, machine-learning processes as described in this disclosure may be used to generate machine-learning models 224. A "machine-learning model," as used in this disclosure, is a mathematical and/or algorithmic representation of a relationship between inputs and outputs, as generated using any machine-learning process including without limitation any process as described above and stored in memory; an input is submitted to a machine-learning model 224 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 224 may be generated by creating an artificial neural network, such as a convolutional neural network comprising an input layer of nodes, one or more intermediate layers, and an output layer of nodes. Connections between nodes may be created via the process of "training" the network, in which elements from a training data 204 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. A machine-learning model may be used to derive numerical scales for providing numerical values to dental parameter 112 and/or dental index 160, and the like, as described above, to "learn" the upper and lower limits to the numerical scale, the increments to providing scoring, and the criteria for increasing and decreasing elements encompassed in the dental parameter 112 and/or dental index 160, and the like. A machine-learning model may be used to "learn" which elements of dental factors 108 have what effect on dental parameter 112, and which elements of dental parameter 112 are affected by particular alimentary elements 144 and the magnitude of effect, and the like. The magnitude of the effect may be enumerated and provided as part of system 100, where alimentary elements 144 are communicated to subject for their degradation reduction properties.

Still referring to FIG. 2, machine-learning algorithms may include at least a supervised machine-learning process 228. At least a supervised machine-learning process 228, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include a dental parameter 112 (potentially classified into dental groupings 120), as described above as inputs, alimentary element 144 outputs, and a ranking function representing a desired form of relationship to be detected between inputs and outputs; ranking function may, for instance, seek to maximize the probability that a given input (such as alimentary levels 136) and/or combination of inputs is associated with a given output (dental nourishment program 156 that incorporate alimentary element 144 to achieve alimentary levels 136 that are 'best' for dental grouping 120) to minimize the probability that a given input is not associated with a given output, for instance finding the most suitable times to consume meals, and what the meals should be, and the like. Ranking function may be expressed as a risk function representing an "expected loss" of an algorithm relating inputs to outputs, where loss is computed as an error function representing a degree to which a prediction generated by the relation is incorrect when compared to a given input-output pair provided in training data 204. Persons skilled in the art, upon the benefit of reviewing the entirety of this disclosure, will be aware of various possible variations of at least a supervised machine-learning process 228 that may be used to determine relation between inputs and outputs. Supervised machine-learning processes may include classification algorithms as defined above.

Further referring to FIG. 2, machine learning processes may include at least an unsupervised machine-learning process 232. An unsupervised machine-learning process 232, as used herein, is a process that derives inferences in datasets without regard to labels; as a result, an unsupervised machine-learning process 232 may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 2, machine-learning module 200 may be designed and configured to create a machine-learning model 224 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 2, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Still referring to FIG. 2, models may be generated using alternative or additional artificial intelligence methods, including without limitation by creating an artificial neural network, such as a convolutional neural network comprising an input layer of nodes, one or more intermediate layers, and an output layer of nodes. Connections between nodes may be created via the process of "training" the network, in which elements from a training data 204 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. This network may be trained using training data 204.

Figure 3:
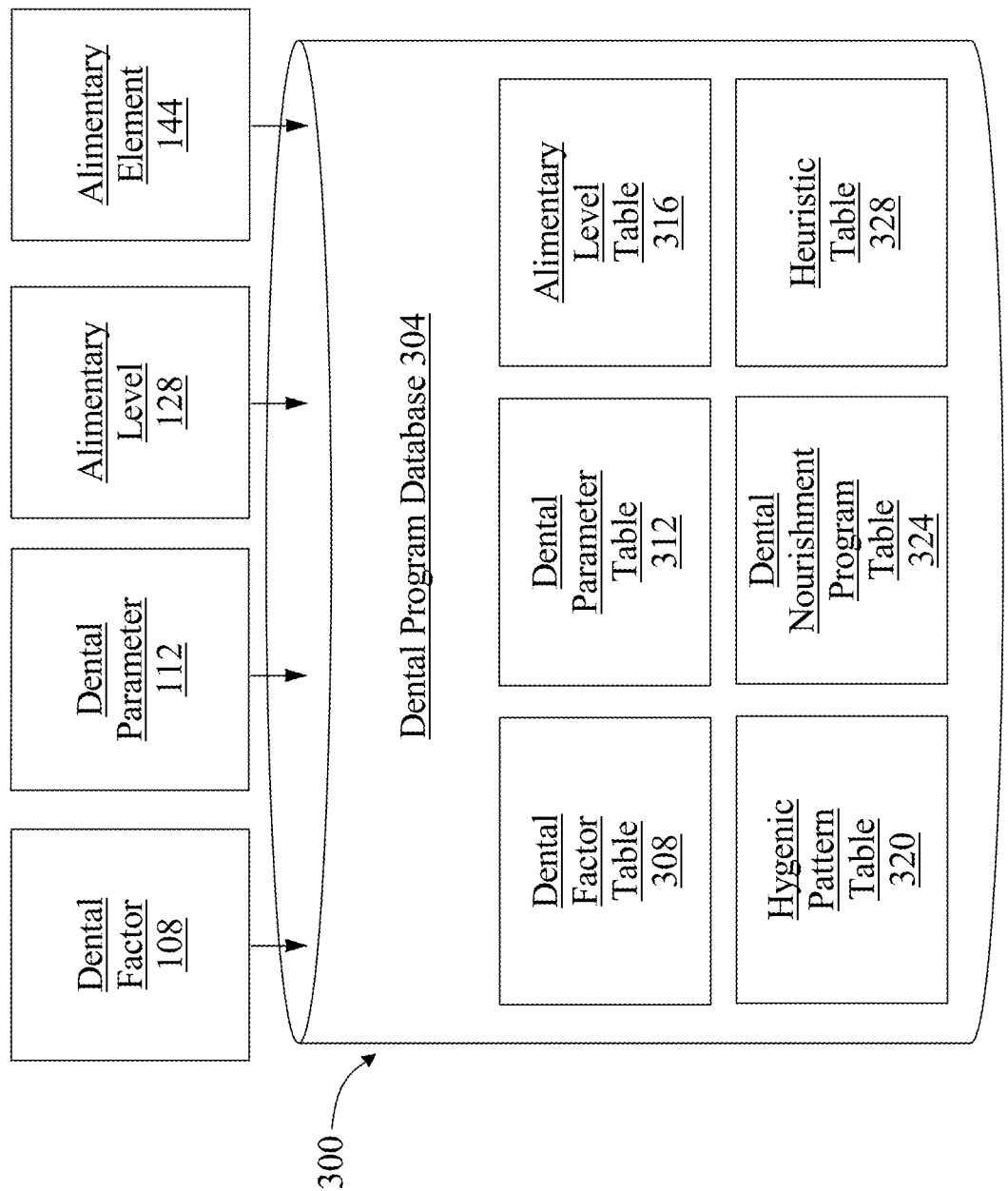
FIG. 3 is a block diagram of an exemplary embodiment of a dental program database.

Referring now to FIG. 3, a non-limiting exemplary embodiment 300 of a dental program database 304 is illustrated. Dental factor(s) 108 from a plurality of subjects, for instance for generating a training data classifier 216, may be stored and/or retrieved in dental program database 304. Dental factor(s) 108 data from a plurality of subjects for generating training data 204 may also be stored and/or retrieved from a dental program database 304. Computing device 104 may receive, store, and/or retrieve training data 204, wearable device data, physiological sensor data, biological extraction data, and the like, from dental program database 304. Computing device 104 may store and/or retrieve dental factor machine-learning model 116, dental classifier 124, among other determinations, I/O data, models, and the like, from dental program database 304.

Continuing in reference to FIG. 3, dental program database 304 may be implemented, without limitation, as a relational database, a key-value retrieval database such as a NOSQL database, or any other format or structure for use as a database that a person skilled in the art would recognize as suitable upon review of the entirety of this disclosure. Dental program database 304 may alternatively or additionally be implemented using a distributed data storage protocol and/or data structure, such as a distributed hash table and the like. Dental program database 304 may include a plurality of data entries and/or records, as described above. Data entries in a dental program database 304 may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a database may store, retrieve, organize, and/or reflect data and/or records as used herein, as well as categories and/or populations of data consistent with this disclosure.

Further referring to FIG. 3, dental program database 304 may include, without limitation, dental factor table 308, dental parameter table 312, alimentary level table 316, hygienic pattern table 320, dental nourishment program table 324, and/or heuristic table 328. Determinations by a machine-learning process, machine-learning model, ranking function, and/or classifier, may also be stored and/or retrieved from the dental program database 304. As a non-limiting example, dental program database 304 may organize data according to one or more instruction tables. One or more dental program database 304 tables may be linked to one another by, for instance in a non-limiting example, common column values. For instance, a common column between two tables of dental program database 304 may include an identifier of a submission, such as a form entry, textual submission, accessory device tokens, local access addresses, metrics, and the like, for instance as defined herein; as a result, a search by a computing device 104 may be able to retrieve all rows from any table pertaining to a given submission or set thereof. Other columns may include any other category usable for organization or subdivision of data, including types of data, names and/or identifiers of individuals submitting the data, times of submission, and the like; persons skilled in the art, upon reviewing the entirety of this disclosure, will be aware of various ways in which data from one or more tables may be linked and/or related to data in one or more other tables.

Continuing in reference to FIG. 3, in a non-limiting embodiment, one or more tables of a dental program database 304 may include, as a non-limiting example, a dental factor table 308, which may include categorized identifying data, as described above, including dental factor 108 data such as genetic data, epigenetic data, microbiome data, physiological data, biological extraction data, biomarker types and concentrations, current nutritional deficiencies, physician assessments, symptom assessment data, diagnoses, and the like. Dental factor table 308 may include dental factor 108 categories according to gene expression patterns, SNPs, mutations, enzyme specific activity and concentration, phosphorylation data, proteasomal degradation data, data concerning metabolism of alimentary elements 144, pharmacokinetics, nutrient absorption, bacterial isolates, and the like. One or more tables may include dental parameter table 312, which may include data regarding dental factor 108, thresholds, scores, metrics, values, categorizations, and the like, that system 100 may use to calculate, derive, filter, retrieve and/or store linked tables to, for instance and without limitation, mathematical expressions that describe the impact of each dental factor 108 datum on dental parameter 112, for instance threshold values for gene expression, and the like, as it relates to dental parameters, symptom manifestation, dental grouping 120, and the like. One or more tables may include alimentary level table 316, which may include data on alimentary levels 136, nutritional metrics, current levels of nutrition in subject, maximal nutrient thresholds, minimal nutrient thresholds, nutrients averages and statistical evaluations among cohorts of subjects, data from alike subjects with similar dental factor 108, dental parameter 112, and the like, that system 100 may use to calculate, derive, filter, retrieve and/or store alimentary elements and/or respective effects 140 according to dental parameters 112, dental grouping 120, and/or alimentary levels 136. One or more tables may include hygienic pattern table 320, which may include functions, model, equations, algorithms, and the like, using to calculate or derive hygienic patterns 152 relating to dental parameter 112 and/or dental grouping 120, may include alimentary elements 144 organized by nutrient, nutrient classification, age of subject, sex, symptom severity, and the like, which may be used to calculate, filter, or otherwise determine therapeutic amounts of nutrients and/or products relating to hygienic patterns and/or alimentary elements. One of more tables may include a dental nourishment program table 324, which may include hygiene products and/or alimentary elements 144 identifiers, frequencies, magnitudes, consumption models regarding times of consumption and/or use, identifiers of meals, recipes, ingredients, diet types, and the like. One or more tables may include, without limitation, a heuristic table 328, which may organize rankings, scores such as dental indexes 148, models such as indexing model 164 and other scoring functions, classifiers, inputs and outputs such as nutritional input and weighting factors, functions, numerical values, scales, arrays, matrices, and the like, that represent determinations, probabilities, metrics, parameters, values, and the like, include one or more inputs describing potential mathematical relationships, as described herein.

Figure 4A:
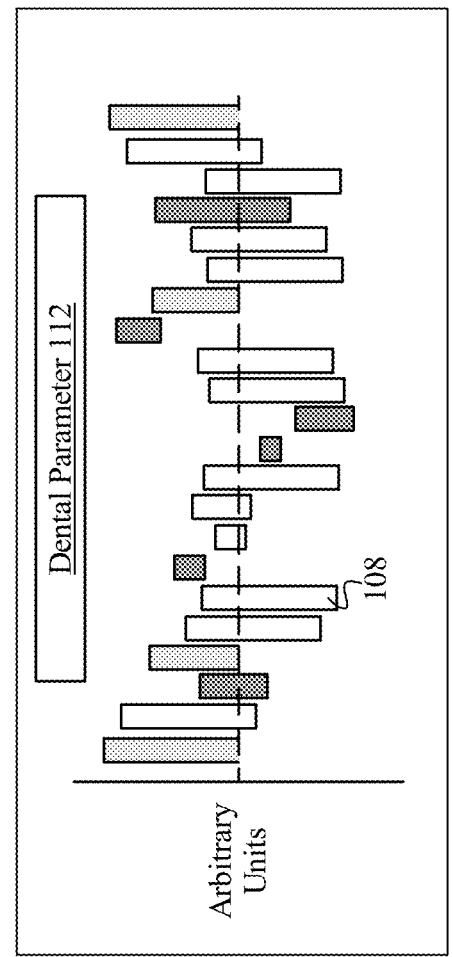
FIGS. 4A and 4B are a diagrammatic representations of an exemplary embodiment of a dental parameter.
Figure 4B:
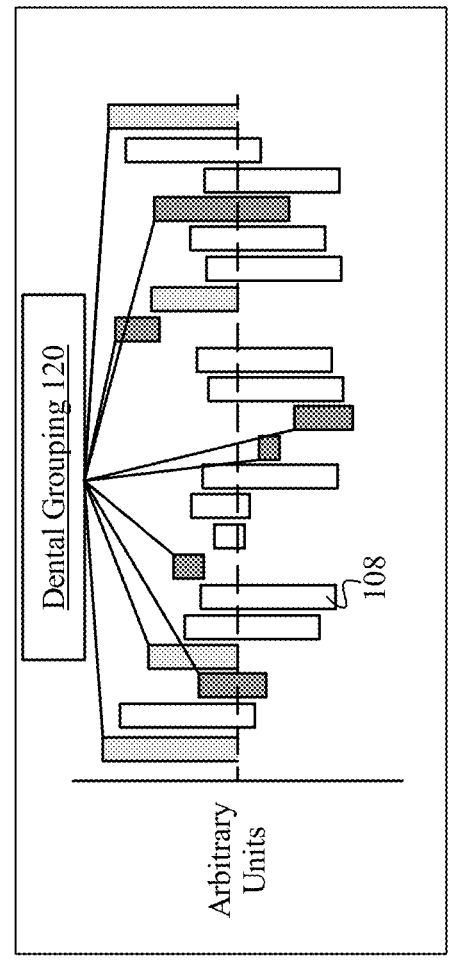

Referring now to FIG. 4A, a non-limiting exemplary embodiment 400 of a dental parameter 112 is illustrated. Dental parameter 112 may include a variety of dental factor 108 categories, for instance 22 distinct categories, as shown in FIGS. 4A and 4B. Each dental factor 108 may be assigned a value, such as an arbitrary value, where some dental factors 108, such as those shaded in light grey, may relate to absolute scales from [0, x], where x is a maximal value and the range of values for the dental factor 108 cannot be below a 'zero amount'. Some dental factors 108, such as those shaded in dark grey, may relate to gene expression levels, wherein, the dental factor 108 is enumerated as a 'box plot' that illustrates the range of expression in a population of subjects organized according to, for instance tissue type. In such an example, the dashed line may relate to a 'normal threshold' above which is elevated gene expression, below which is decreased expression level. Each dental factor 108 may have associated with it a numerical score, or some other identifying mathematical value that computing device 104 may assign. Persons skilled in the art, upon the benefit of this disclosure in its entirety, may appreciate that for each subject, any number of dental factors 108 may be enumerated and assigned a value according to dental factor machine-learning model 116. Dental parameter 112 may be graphed, or otherwise displayed, according to the enumeration by dental factor machine-learning model 116. Each bar of the bar graph, or combinations of bar graph categories, may instruct classification of a subject's dental parameter 112 to a dental grouping 120.

Referring now to FIG. 4B, in non-limiting exemplary illustrations dental parameter 112 may be classified to a dental grouping 120. Some and/or all of the dental factors 108 summarized in dental parameter 112 may be used to classify an individual to a particular dental grouping 120. For instance, as shown in FIG. 4B, ten of the 22 dental factor 108 categories may be used to classify dental parameter 112 to one or more dental groupings 124. Alternatively or additionally, dental factor machine-learning model 116 may be trained to assign dental factor 108 to a dental grouping 120, wherein computing device 104 may derive the identity of dental grouping 120 according to which dental grouping 120 has the most identifying data points. Alternatively or additionally, dental classifier 124 may be trained to assign subject to a dental grouping 120 according to patterns observed in dental factors 108, for instance according to data from a subset of subjects.

Figure 5:
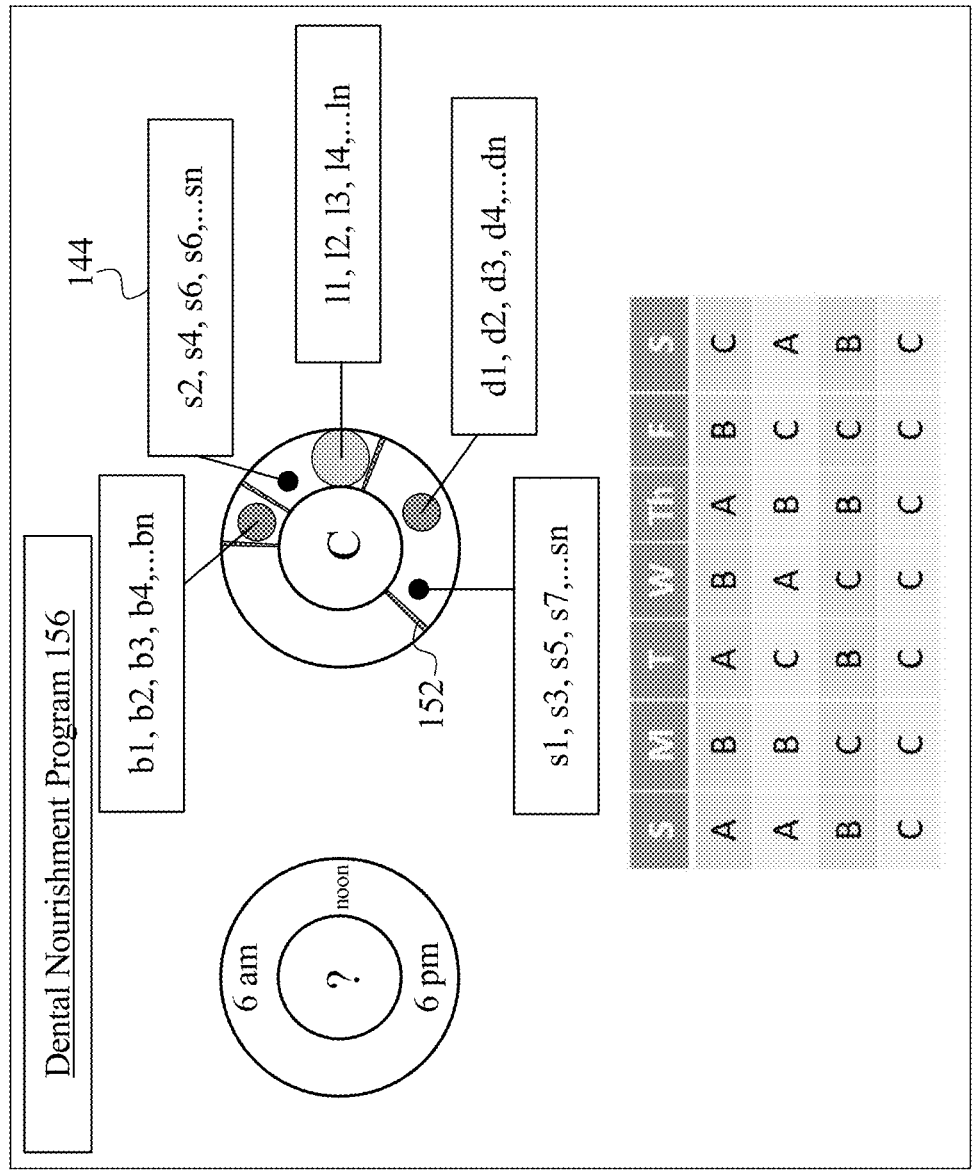
FIG. 5 is a diagrammatic representation of an exemplary embodiment of a dental nourishment program.

Referring now to FIG. 5, a non-limiting exemplary embodiment 500 of a dental nourishment program 156 is illustrated. Dental nourishment program 156 may include a schedule for arranging outputs from alimentary model 132 and hygienic model including alimentary elements 144 and hygienic patterns 152, according to for instance a 24-hour timetable, as designated on the left, where consumption and hygiene is planned along a subject's typical day-night cycle, beginning at ~6 am until just after 6 pm. In this way, the importance of providing regularly scheduled mealtimes may help provide normalcy to the subject's circadian rhythm which may be important, especially in maintaining tightly regulated alimentary levels 136. Alimentary element 144 may include breakfast (denoted as mid-sized dark grey circle), which may correspond to a file of breakfast-related plurality of alimentary elements 144 (denoted b1, b2, b3, b4 . . . bn, to the nth breakfast item). Alimentary element 144 may include snacks eaten throughout the day to, for instance achieve alimentary levels 136 missing from meals (denoted as small black circles), which may correspond to a file of snacking-related plurality of alimentary elements 144 (denoted s1, s2, s3, s4 . . . sn, to the nth snacking item). Alimentary element 144 may include dinner (denoted as large-sized light grey circle), which may correspond to a file of dinner-related plurality of alimentary elements 144 (denoted d1, d2, d3, d4 . . . dn, to the nth dinner item). Hygienic patterns 152 may relate to a series of tasks such as drinking fluorinated water after meals, brushing teeth, flossing, mouthwash use, and the like, as designated along the time scale as dark grey wedges. Dental nourishment program 156 may include a variety of diets and/or hygienic patterns 152, as denoted in the monthly schedule at the bottom, Sunday through Saturday. Dental nourishment program 156 'C' is shown, which may be an idealistic goal for subject to achieve by the end of the month, where nourishment plan 'A' and 'B' are intermediate plans intended to wean subject to the 'ideal' plan. Alternatively or additionally, plans may be based around the scheduling of oral surgeries, orthodontics, and the like, where short-term (on the order of days, after wisdom teeth removal) or longer-term (on the order of years, such as wearing braces and/or headgear) scheduling is adopted. Alimentary elements 144 may be classified by 'meal type' may be further modified by 'A' and 'B' according to subject preferences 148 collected by computing device 104 throughout the process. Circle sizes, denoting alimentary element 144 classes may relate to magnitude, which are graphed along the circle corresponding to the frequency they are expected to be consumed. Subject may indicate which alimentary element 144 from each category was consumed, and when it was consumed, as inputs to calculate at dental index 160 according to an indexing model 164.

Figure 6:
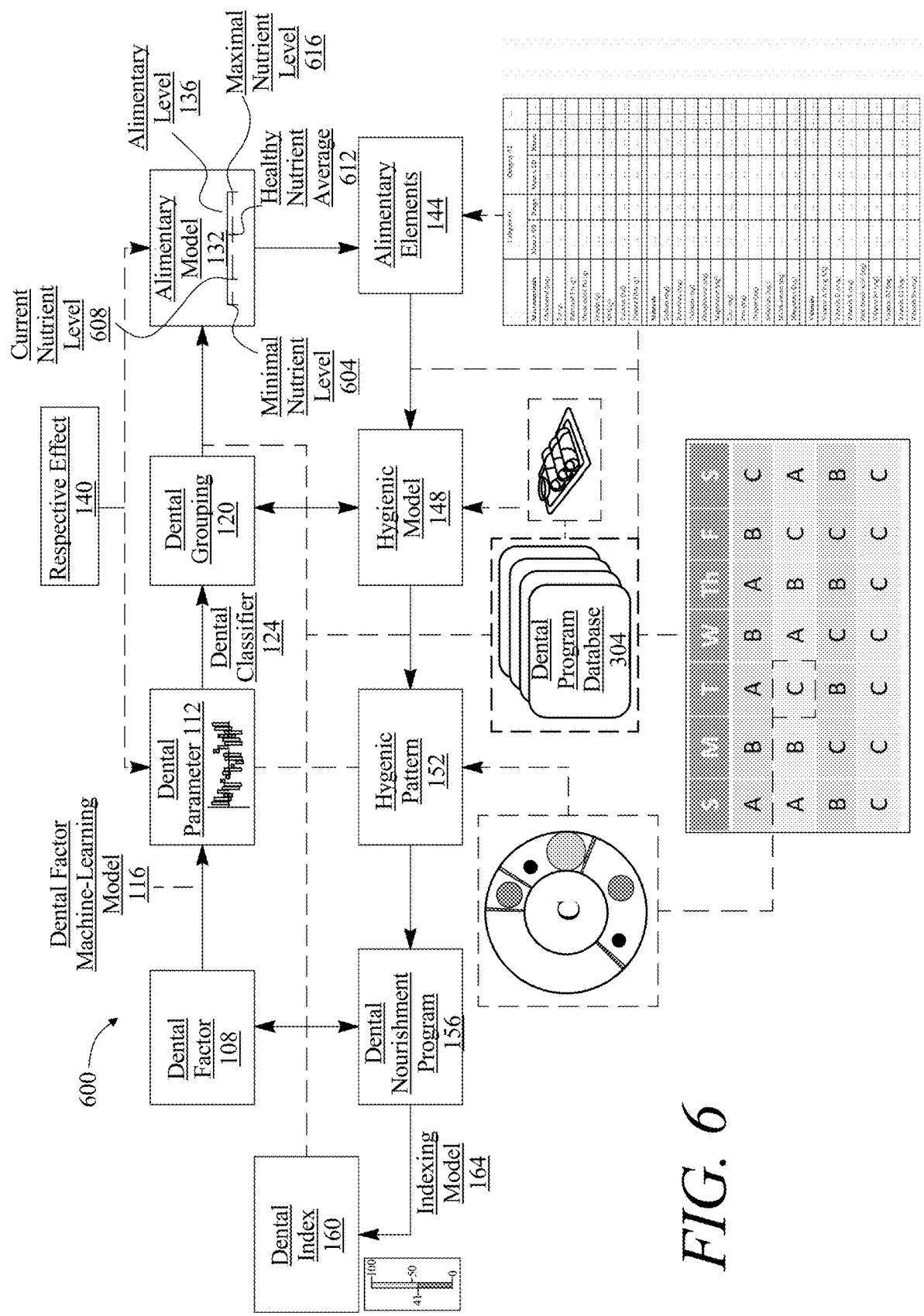
FIG. 6 is a diagrammatic representation of an exemplary embodiment of an overview of a dental nourishment program.

Referring now to FIG. 6, a non-limiting exemplary embodiment 600 of an overview of generating a dental nourishment program 156 is illustrated. Computing device 104 may receive dental factor(s) 108 and generate dental factor machine-learning model 116 to derive equations and/or scoring functions from training data to output dental parameter(s) 112. Computing device 104 may generate a dental classifier 124 to automatedly classify a subject's dental parameter(s) 112 to a dental grouping 120, such as a determination about the type of dental disorder, condition, tooth pain, among other classifications. Classification may include identifying a nutrition-linked pain disorder category, which may uncover an etiology for dental issue in the subject that is indicative of a nutritional deficiency, nutritional surplus, or some other inconsistency in nutrition from what is considered 'healthy' or otherwise necessary on a per-subject basis. Computing device 104 may then determine a plurality of alimentary levels 136, for instance and without limitation, which relate to nutritional metrics such as minimal nutrient level 604, current nutrient level 608, healthy nutrient average 612, and/or maximal nutrient level 616. Such alimentary level(s) 136 may be used as inputs with dental parameter(s) 112 to generate an output of a respective effect 140, which may include a relationship between the current nutrient level and the rate of tooth decay, tooth color, oral sores, and the like, a subject experiences. Alimentary levels 136 may be used as inputs for computing device 104 to output alimentary elements 144, which may include a therapeutic amount of a nutrient and/or nutrient combination intended to address pain and/or discomfort.

Still referring to FIG. 6, alimentary level 140 may be stored and/or retrieved from a database, such as dental program database 304, as described herein. Computing device 104 may use alimentary level 140 as an input to determine alimentary element(s) 128. Alimentary elements 144 may be stored and/or retrieved from dental program database 304. Computing device 104 may generate a hygienic model 148 to observe relationships in training data between dental outcomes and dental product use alongside dietary patterns to derive equations, functions, and the like, which may be used to output hygienic patterns 152. Computing device 104 may accept alimentary elements 144 as inputs, along with constraints imposed from subject preferences, frequencies and magnitudes associated with maintain minimal and/or maximal acceptable alimentary levels 136, and hygienic patterns 152 to generate an objective functions, such as a linear programming function, which can output at least an ordering of the plurality of alimentary elements 144 according to the constraints Orderings of plurality of alimentary elements 144 and hygienic patterns 152 may be stored and/or retrieved from dental program database 304. Computing device 104 may then, using the ordered plurality of alimentary elements 144 and hygienic patterns 152, generate a dental nourishment program 156. Dental nourishment program 156 may include alimentary elements 128 and dental hygiene instructions thoughtfully curated according to daily schedules, including magnitudes, frequencies, and food ordering information, including recipes if meals with be made by subject. Computing device 104 may provide a dental index 160 by generating an indexing model 164 for providing the subject a scoring criteria and a numerical assessment of the improvement and/or deterioration of dental health. Such a dental index 160 may increase with adherence and participation in dental nourishment program 156, including providing new up-to-date dental factor 108 data and providing nutritional input. Dental index 160 may include thresholds indicating when dental work should be performed, such as regular scheduled cleanings.

Figure 7:
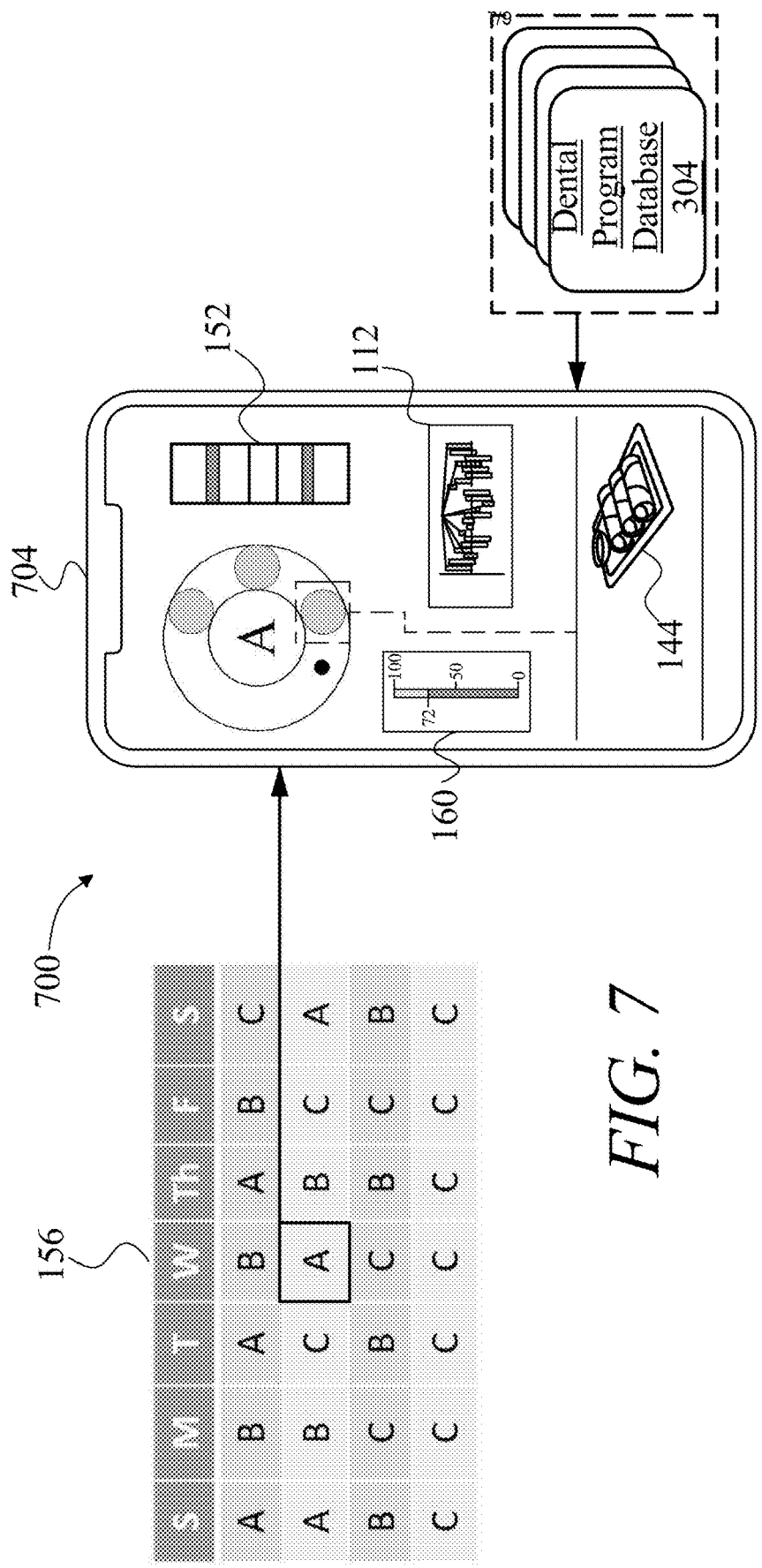
FIG. 7 is a diagrammatic representation of an exemplary embodiment of a client device.

Referring now to FIG. 7, a non-limiting exemplary embodiment 700 of a client device 704 is illustrated. Client device 704 may include computing device 104, a "smartphone," cellular mobile phone, desktop computer, laptop, tablet computer, internet-of-things (IOT) device, wearable device, among other devices. Client device 704 may include any device that is capable for communicating with computing device 104, dental program database 304, or able to receive, transmit, and/or display, via a graphical user interface, dental parameter 112, alimentary element 144, hygienic patterns 152, dental nourishment program 156, dental index 160, among other outputs from system 100. Client device 704 may provide a dental parameter 112, for instance as a collection of metrics determined from dental factor 108 data. Client device 704 may provide dental grouping 120 that was determined as a function of dental classifier 124 and dental parameter 112. Client device 704 may provide data concerning alimentary levels 136, including the levels of specific nutrients, nutrient ranges, nutrients to avoid, and the like. Client device 704 may link timing of foods to preemptive ordering interface for ordering a alimentary element 144, for instance and without limitation, through a designated mobile application, mapping tool or application, and the like, and a radial search method, or any other locating method, about a subject's current location as described in U.S. Nonprovisional application Ser. No. 17/087,745, filed Nov. 3, 2020, titled "A METHOD FOR AND SYSTEM FOR PREDICTING ALIMENTARY ELEMENT ORDERING BASED ON BIOLOGICAL EXTRACTION," the entirety of which is incorporated herein by reference. Client device 704 may display alimentary element 144 as a function of location and biological extraction data, for instance and without limitation, as described in the incorporated reference. Client device 704 may link nourishment consumption program 120 to a scheduling application, such as a 'calendar' feature on client device, which may set audio-visual notifications, timers, alarms, and the like, to assist subject in maintaining optimal alimentary levels 136.

Figure 8:
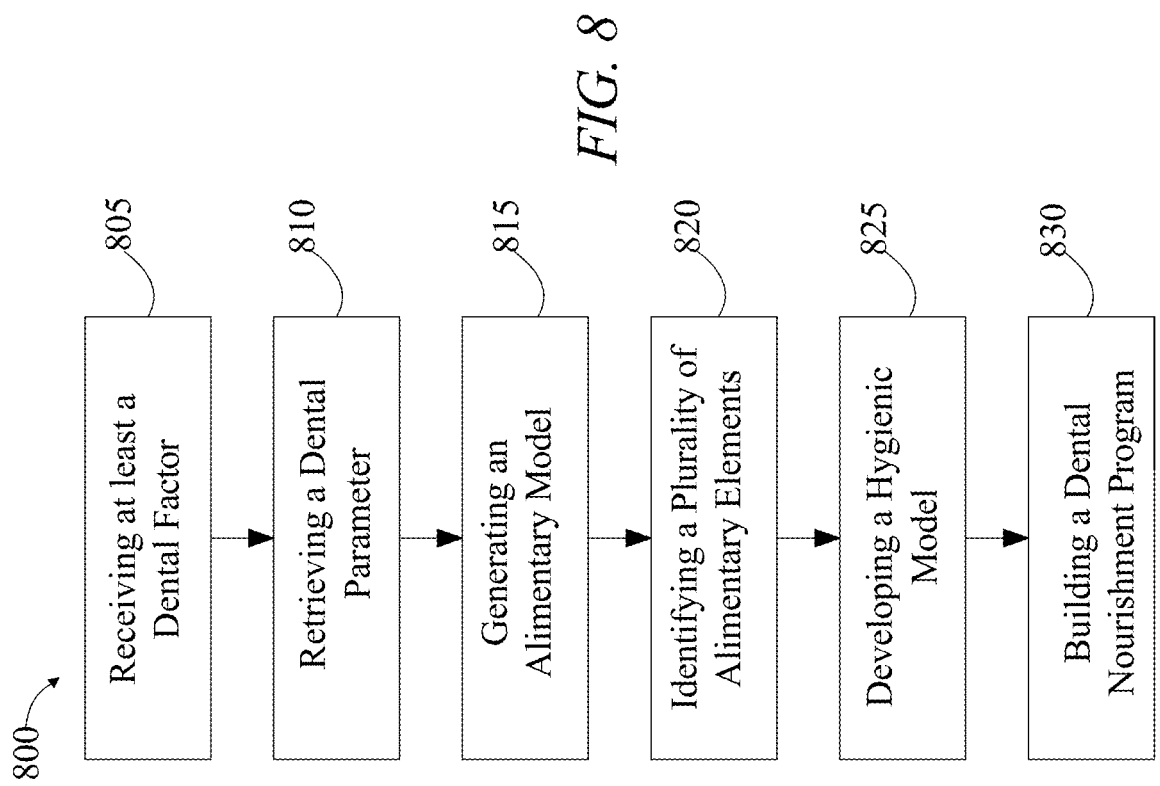
FIG. 8 is a flow diagram of an exemplary embodiment of a method for generating a dental nourishment program.

Referring now to FIG. 8, an exemplary embodiment 800 of a method for generating a dental nourishment program 156 is illustrated. At step 805, the method includes receiving, by a computing device 104, at least a dental factor 108 relating to a subject; this may be implemented, without limitation, as described above in FIGS. 1-7.

Still referring to FIG. 8, at step 810, method includes retrieving, by the computing device 104, using the dental factor 108, a dental parameter 112 related to the subject. Retrieving the dental parameter 112 related to the subject may include training a dental factor machine-learning model 116 with training data including a plurality of data entries correlating dental factors to dental parameters and generating the dental parameter 112 as a function of the dental factor machine-learning model 116 and the at least a dental factor 108. Retrieving the dental parameter 112 related to the subject may include training a dental factor machine-learning model 116 with training data including a plurality of data entries correlating dental factors to dental parameters and generating the dental parameter 112 as a function of the dental factor machine-learning model 116 and the at least a dental factor 108. Retrieving the dental parameter 112 may include training a dental classifier 124 using a dental classification machine-learning process and training data including a plurality of data entries of dental parameter data from a subset of categorized subjects and classifying the dental parameter 112 to a dental grouping 120 using the dental classifier 124. Classifying may include classifying the dental parameter 112 to a nutrition-linked dental grouping; this may be implemented, without limitation, as described above in FIGS. 1-7.

Continuing in reference to FIG. 8, at step 815, method includes generating, by the computing device 104, using the dental parameter 112, an alimentary model 132, wherein generating the alimentary model 132 includes determining a respective effect 140 of each alimentary level 140 of a plurality of alimentary levels 136 on the dental parameter 112 and generating the alimentary model 132 as a function of the respective effect 140 of the plurality of alimentary levels 136. Generating the alimentary model 132 may include training the alimentary model 132 using training data including a plurality of data entries correlating the plurality of alimentary levels to respective effects on dental parameters and generating the alimentary model 132 as a function of the training. Determining a respective effect 140 of each alimentary level 140 of the plurality of alimentary levels 136 may include retrieving the respective effect 140 of each alimentary level 140 on the dental parameter 112 as a function of at least the dental factor 108; this may be implemented, without limitation, as described above in FIGS. 1-7.

Continuing in reference to FIG. 8, at step 820, method includes identifying, by the computing device 104, using the alimentary model 132, a plurality of alimentary elements 144. Identifying the plurality of alimentary elements 144 may include retrieving the plurality of alimentary elements 144 as a function of the dental grouping 120; this may be implemented, without limitation, as described above in FIGS. 1-7.

Continuing in reference to FIG. 8, at step 825, method includes developing, by the computing device 104, using plurality of alimentary elements 144, a hygienic model 148, wherein developing the hygienic model 148 includes determining, using the plurality of alimentary elements 144, a plurality of hygienic patterns 152 relating dental hygiene in relation to consumption of the plurality of alimentary elements 144 and developing the hygienic model 148 as a function of the hygienic patterns 152 and the plurality of alimentary elements 144. Generating the hygienic model 148 may include generating a linear programming function with the at least the plurality of alimentary elements wherein the linear programming function outputs at least an ordering of a plurality of alimentary elements 144 according to constraints from a plurality of hygienic patterns 152; this may be implemented, without limitation, as described above in FIGS. 1-7.

Continuing in reference to FIG. 8, at step 830, method includes building, by the computing device 104, a dental nourishment program 156 using the alimentary model 132 and the hygienic model 148. Dental nourishment program may include a dental index. Generating the dental index may include receiving nutritional input from the subject, generating an indexing model using training data including a plurality of data entries correlating the respective effect of each alimentary element on the dental parameter and generating the dental index as a function of the indexing model and the nutritional input.

It is to be noted that any one or more of the aspects and embodiments described herein may be conveniently implemented using one or more machines (e.g., one or more computing devices that are utilized as a user computing device for an electronic document, one or more server devices, such as a document server, and the like) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, and the like), a magneto-optical disk, a read-only memory "ROM" device, a random-access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, and the like), a web appliance, a network router, a network switch, a network bridge, any machine capable of executing a sequence of instructions that specify an action to be taken by that machine, and any combinations thereof. In one example, a computing device may include and/or be included in a kiosk.

Figure 9:
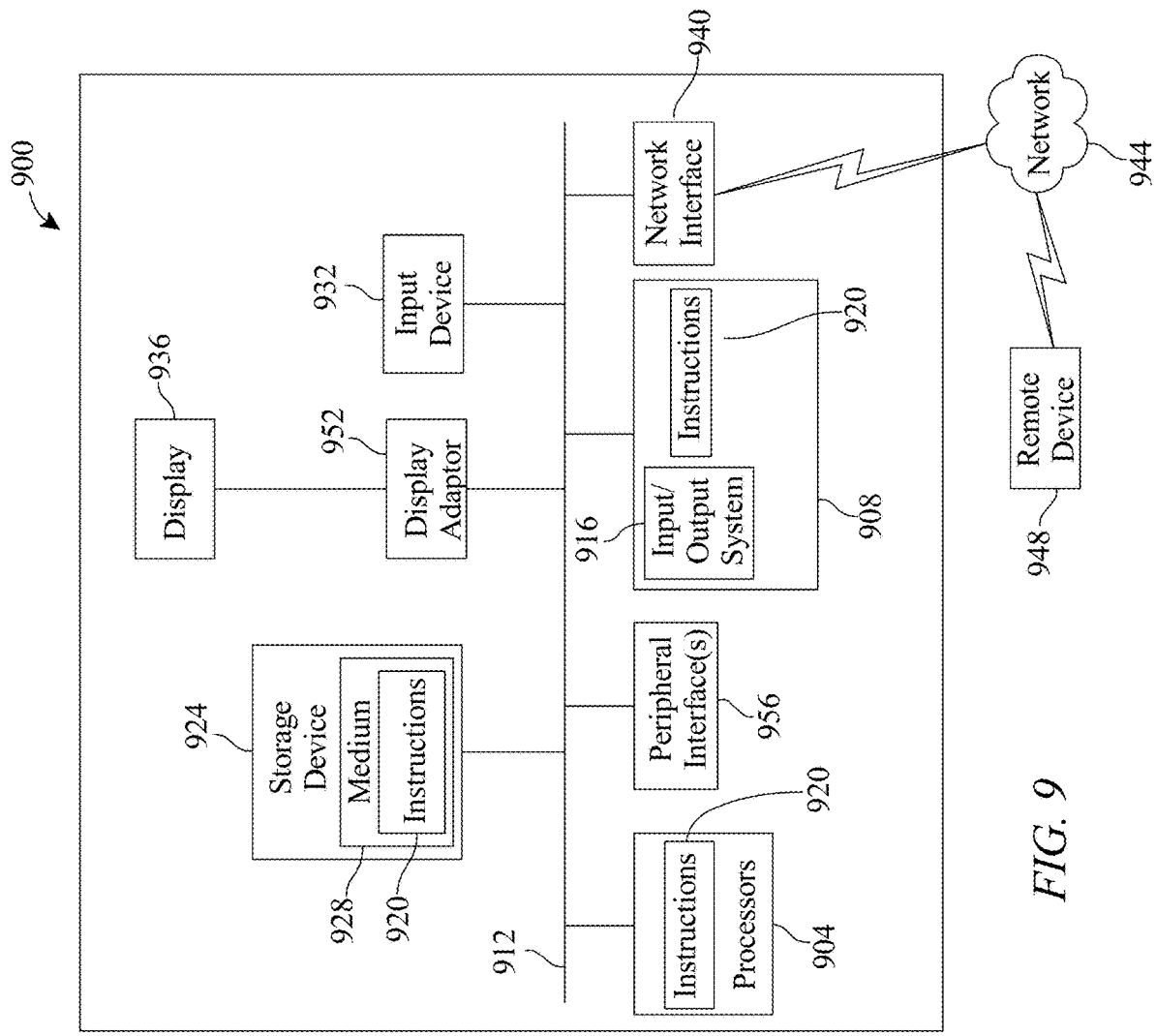
FIG. 9 is a block diagram of a computing system that can be used to implement any one or more of the methodologies disclosed herein and any one or more portions thereof.

FIG. 9 shows a diagrammatic representation of one embodiment of a computing device in the exemplary form of a computer system 900 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 900 includes a processor 904 and a memory 908 that communicate with each other, and with other components, via a bus 912. Bus 912 may include any of several types of bus structures including, but not limited to, a memory bus, a memory controller, a peripheral bus, a local bus, and any combinations thereof, using any of a variety of bus architectures.

Processor 904 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 904 may be organized according to Von Neumann and/or Harvard architecture as a non-limiting example. Processor 904 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating-point unit (FPU), and/or system on a chip (SoC).

Memory 908 may include various components (e.g., machine-readable media) including, but not limited to, a random-access memory component, a read only component, and any combinations thereof. In one example, a basic input/output system 916 (BIOS), including basic routines that help to transfer information between elements within computer system 900, such as during start-up, may be stored in memory 908. Memory 908 may also include (e.g., stored on one or more machine-readable media) instructions (e.g., software) 920 embodying any one or more of the aspects and/or methodologies of the present disclosure. In another example, memory 908 may further include any number of program modules including, but not limited to, an operating system, one or more application programs, other program modules, program data, and any combinations thereof.

Computer system 900 may also include a storage device 924. Examples of a storage device (e.g., storage device 924) include, but are not limited to, a hard disk drive, a magnetic disk drive, an optical disc drive in combination with an optical medium, a solid-state memory device, and any combinations thereof. Storage device 924 may be connected to bus 912 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 924 (or one or more components thereof) may be removably interfaced with computer system 900 (e.g., via an external port connector (not shown)). Particularly, storage device 924 and an associated machine-readable medium 928 may provide nonvolatile and/or volatile storage of machine-readable instructions, data structures, program modules, and/or other data for computer system 900. In one example, software 920 may reside, completely or partially, within machine-readable medium 928. In another example, software 920 may reside, completely or partially, within processor 904.

Computer system 900 may also include an input device 932. In one example, a user of computer system 900 may enter commands and/or other information into computer system 900 via input device 932. Examples of an input device 932 include, but are not limited to, an alpha-numeric input device (e.g., a keyboard), a pointing device, a joystick, a gamepad, an audio input device (e.g., a microphone, a voice response system, and the like), a cursor control device (e.g., a mouse), a touchpad, an optical scanner, a video capture device (e.g., a still camera, a video camera), a touchscreen, and any combinations thereof. Input device 932 may be interfaced to bus 912 via any of a variety of interfaces (not shown) including, but not limited to, a serial interface, a parallel interface, a game port, a USB interface, a FIREWIRE interface, a direct interface to bus 912, and any combinations thereof. Input device 932 may include a touch screen interface that may be a part of or separate from display 936, discussed further below. Input device 932 may be utilized as a user selection device for selecting one or more graphical representations in a graphical interface as described above.

A user may also input commands and/or other information to computer system 900 via storage device 924 (e.g., a removable disk drive, a flash drive, and the like) and/or network interface device 940. A network interface device, such as network interface device 940, may be utilized for connecting computer system 900 to one or more of a variety of networks, such as network 944, and one or more remote devices 948 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus, or other relatively small geographic space), a telephone network, a data network associated with a telephone/voice provider (e.g., a mobile communications provider data and/or voice network), a direct connection between two computing devices, and any combinations thereof. A network, such as network 944, may employ a wired and/or a wireless mode of communication. In general, any network topology may be used. Information (e.g., data, software 920, and the like) may be communicated to and/or from computer system 900 via network interface device 940.

Computer system 900 may further include a video display adapter 952 for communicating a displayable image to a display device, such as display device 936. Examples of a display device include, but are not limited to, a liquid crystal display (LCD), a cathode ray tube (CRT), a plasma display, a light emitting diode (LED) display, and any combinations thereof. Display adapter 952 and display device 936 may be utilized in combination with processor 904 to provide graphical representations of aspects of the present disclosure. In addition to a display device, computer system 900 may include one or more other peripheral output devices including, but not limited to, an audio speaker, a printer, and any combinations thereof. Such peripheral output devices may be connected to bus 912 via a peripheral interface 956. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions, and additions may be made to that which is specifically disclosed herein without departing from the spirit and scope of the present invention.

What is claimed is:

1. A system for generating a dental nourishment program using machine-learning, the system comprising a computing device, wherein the computing device is configured to:
   receive at least a dental factor relating to a subject;
   retrieve, using the at least a dental factor, a dental parameter related to the subject, wherein retrieving the dental parameter related to the subject further comprises:
   receiving training data, wherein the training data comprises a plurality of data entries correlating the dental factors as inputs to the dental parameters as outputs
   iteratively training a dental factor machine-learning model using the training data, wherein iteratively training the dental factor machine-learning model comprises:
   updating the training data as a function of inputs and outputs of a previous iteration of the dental factor machine-learning model; and
   retraining the dental factor machine-learning model using the updated training data; and
   generate, using the dental parameter, an alimentary model, wherein the alimentary model is a machine learning model trained using alimentary training data configured to correlate the dental parameters generated as a function of the trained dental factor machine-learning model to alimentary element subjects, wherein generating the alimentary model further comprises:
   determining a respective effect of each alimentary level of a plurality of alimentary levels on the dental parameter; and
   generating the alimentary model as a function of the respective effect of the plurality of alimentary levels;
   identify, using the alimentary model, a plurality of alimentary elements, wherein the plurality of alimentary elements relates to dietary data;
   modify the plurality of alimentary elements as a function of a received subject preference, wherein the subject preference comprises at least one constraint on the plurality of alimentary elements;
   develop, using the modified plurality of alimentary elements, a hygienic model, wherein developing the hygienic model includes:
   determining, using the modified plurality of alimentary elements, a plurality of hygienic patterns relating dental hygiene in relation to consumption of the plurality of alimentary elements; and
   developing the hygienic model as a function of the hygienic patterns and the modified plurality of alimentary elements; and
   build a dental nourishment program as a function of the modified plurality of alimentary elements and the hygienic model using the alimentary model, wherein building the dental nourishment program further comprises:
   generating a linear programming function with the plurality of alimentary elements, wherein the linear programming function outputs at least an ordering of the modified plurality of alimentary elements according to the at least one constraint from the subject preference.

2. The system of claim 1, wherein generating the alimentary model further comprises:
   training a dental classifier using a dental classification machine-learning process and training data including a plurality of data entries of dental parameter data from a subset of categorized subjects;
   classifying the dental parameter to a dental grouping using the dental classifier; and
   generating the alimentary model as a function of the dental grouping.

3. The system of claim 2, wherein classifying the dental parameter includes classifying the dental parameter to a nutrition-linked dental grouping.

4. The system of claim 1, wherein generating the alimentary model further comprises:
   training the alimentary model using alimentary training data including a plurality of data entries correlating the plurality of alimentary levels to respective effects on dental parameters; and
   generating the alimentary model as a function of the training.

5. The system of claim 1, wherein determining a respective effect of each alimentary level of the plurality of alimentary levels further comprises retrieving the respective effect of each alimentary level on the dental parameter as a function of at least the dental factor.

6. The system of claim 1, wherein the computing device is further configured to:
   develop, using the plurality of alimentary elements, a hygienic model, wherein developing the hygienic model includes:
   determining, using the plurality of alimentary elements, a plurality of hygienic patterns relating dental hygiene in relation to consumption of the plurality of alimentary elements; and
   developing the hygienic model as a function of the hygienic patterns and the plurality of alimentary elements; and
   build the dental nourishment program using the alimentary model and the hygienic model.

7. The system of claim 1, wherein the dental nourishment program includes a dental index.

8. The system of claim 7, wherein generating the dental index further comprises:
   receiving nutritional input from the subject;
   generating an indexing model using index training data including a plurality of data entries correlating the respective effect of each alimentary element on the dental parameter; and
   generating the dental index as a function of the indexing model and the nutritional input.

9. A method for generating a dental nourishment program using machine-learning, the method comprising:
   receiving, by a computing device, at least a dental factor relating to a subject;
   retrieving, by the computing device, using the dental factor, a dental parameter related to the subject, wherein retrieving the dental parameter related to the subject further comprises:
   receiving training data, wherein the training data comprises a plurality of data entries correlating the dental factors as inputs to the dental parameters as outputs
   iteratively training a dental factor machine-learning model using the training data, wherein iteratively training the dental factor machine-learning model comprises:
   updating the training data as a function of inputs and outputs of a previous iteration of the dental factor machine-learning model; and
   retraining the dental factor machine-learning model using the updated training data; and
   generating, by the computing device, using the dental parameter, an alimentary model, wherein the alimentary model is a machine learning model trained using alimentary training data configured to correlate the dental parameters generated as a function of the trained dental factor machine-learning model to alimentary element subjects, wherein generating the alimentary model further comprises:

determining a respective effect of each alimentary level of a plurality of alimentary levels on the dental parameter; and generating the alimentary model as a function of the respective effect of the plurality of alimentary levels;

identifying, by the computing device, using the alimentary model, a plurality of alimentary elements;

modifying, by the computing device, the plurality of alimentary elements as a function of a received subject preference, wherein the subject preference comprises at least one constraint on the plurality of alimentary elements;

developing, by the computing device, using the modified plurality of alimentary elements, a hygienic model, wherein developing the hygienic model includes:

determining, using the modified plurality of alimentary elements, a plurality of hygienic patterns relating dental hygiene in relation to consumption of the modified plurality of alimentary elements; and developing the hygienic model as a function of the hygienic patterns and the modified plurality of alimentary elements; and building, by the computing device, a dental nourishment program as a function of the modified plurality of alimentary elements using the alimentary model and the hygienic model, wherein building the dental nourishment program further comprises:

generating a linear programming function with the modified plurality of alimentary elements, wherein the linear programming function outputs at least an ordering of the modified plurality of alimentary elements according to the at least one constraint from the subject preference.

10. The method of claim 9, wherein generating the alimentary model further comprises:

training a dental classifier using a dental classification machine-learning process and training data including a plurality of data entries of dental parameter data from a subset of categorized subjects;

classifying the dental parameter to a dental grouping using the dental classifier; and generating the alimentary model as a function of the dental grouping.

11. The method of claim 10, wherein classifying includes classifying the dental parameter to a nutrition-linked dental grouping.

12. The method of claim 9, wherein generating the alimentary model further comprises:

training the alimentary model using alimentary training data including a plurality of data entries correlating the plurality of alimentary levels to respective effects on dental parameters; and generating the alimentary model as a function of the training.

13. The method of claim 9, wherein determining a respective effect of each alimentary level of the plurality of alimentary levels further comprises retrieving the respective effect of each alimentary level on the dental parameter as a function of at least the dental factor.

14. The method of claim 9 further comprising:

developing, using the plurality of alimentary elements, a hygienic model, wherein developing the hygienic model includes:

determining, using the plurality of alimentary elements, a plurality of hygienic patterns relating dental hygiene in relation to consumption of the plurality of alimentary elements; and developing the hygienic model as a function of the hygienic patterns and the plurality of alimentary elements; and building the dental nourishment program using the alimentary model and the hygienic model.

15. The method of claim 9, wherein the dental nourishment program includes a dental index.

16. The method of claim 15, wherein generating the dental index further comprises:

receiving nutritional input from the subject;

generating an indexing model using index training data including a plurality of data entries correlating the respective effect of each alimentary element on the dental parameter; and generating the dental index as a function of the indexing model and the nutritional input.

* * * * *